United States Patent
Schaal et al.

(10) Patent No.: US 11,371,087 B2
(45) Date of Patent: Jun. 28, 2022

(54) METHODS AND COMPOSITIONS EMPLOYING BLOCKED PRIMERS

(71) Applicant: TAKARA BIO USA, INC., San Jose, CA (US)

(72) Inventors: Thomas D. Schaal, San Jose, CA (US); Jude Menlo Dunne, San Jose, CA (US); Maithreyan Srinivasan, San Jose, CA (US); Alain Mir, San Jose, CA (US)

(73) Assignee: Takara Bio USA, Inc., San Jose, CA (US)

( * ) Notice: Subject to any disclaimer, the term of this patent is extended or adjusted under 35 U.S.C. 154(b) by 129 days.

(21) Appl. No.: 16/091,066

(22) PCT Filed: Jun. 8, 2017

(86) PCT No.: PCT/US2017/036583
§ 371 (c)(1),
(2) Date: Oct. 3, 2018

(87) PCT Pub. No.: WO2017/214417
PCT Pub. Date: Dec. 14, 2017

(65) Prior Publication Data
US 2019/0112648 A1    Apr. 18, 2019

Related U.S. Application Data

(60) Provisional application No. 62/348,428, filed on Jun. 10, 2016.

(51) Int. Cl.
*C12Q 1/6853* (2018.01)
*C12P 19/34* (2006.01)
*C12Q 1/6844* (2018.01)

(52) U.S. Cl.
CPC ............ *C12Q 1/6853* (2013.01); *C12P 19/34* (2013.01); *C12Q 1/6844* (2013.01)

(58) Field of Classification Search
CPC ...... C12Q 1/6853; C12Q 1/6844; C12P 19/34
See application file for complete search history.

(56) References Cited

U.S. PATENT DOCUMENTS

| | | | |
|---|---|---|---|
| 7,833,709 B2 | 11/2010 | Joseph et al. | |
| 8,252,581 B2 | 8/2012 | Joseph et al. | |
| 2007/0281308 A1 | 12/2007 | Zon et al. | |
| 2008/0009007 A1 | 1/2008 | Lyle et al. | |
| 2010/0003724 A1* | 1/2010 | Lebedev | C12Q 1/6869 435/91.2 |
| 2010/0003727 A1 | 1/2010 | Lebedev et al. | |
| 2014/0051848 A1* | 2/2014 | Litosh | C12Q 1/6869 536/26.26 |
| 2014/0065675 A1 | 3/2014 | Chen et al. | |
| 2014/0329245 A1* | 11/2014 | Spier | C12Q 1/6848 435/6.12 |
| 2015/0111789 A1 | 4/2015 | Betts et al. | |
| 2016/0160273 A1* | 6/2016 | Ding | C12Q 1/6844 435/6.12 |
| 2016/0258016 A1 | 9/2016 | Sandberg et al. | |
| 2018/0010176 A1* | 1/2018 | Patel | C12Q 1/6806 |

FOREIGN PATENT DOCUMENTS

| WO | WO2018089550 A1 | 5/2018 |
|---|---|---|
| WO | WO2018152129 A1 | 8/2018 |

OTHER PUBLICATIONS

Shum et al. "Hot Start PCR Update: CleanAmp™ Primers," The Glen Report, May 1, 2009, (May 31, 2009), vol. 21, No. 1, pp. 1-20.

* cited by examiner

*Primary Examiner* — Cynthia B Wilder
(74) *Attorney, Agent, or Firm* — Bret E. Field; Bozicevic, Field & Francis LLP

(57) ABSTRACT

The present disclosure provides methods, compositions, and systems employing blocked primers. Aspects of the disclosure include providing a blocked primer reaction mixture that includes a blocked primer and a template nucleic acid component from a single cell; unblocking the blocked primer to produce an active primer reaction mixture and subjecting the activated primer reaction mixture to primer extension conditions, such as nucleic acid amplification conditions.

21 Claims, 6 Drawing Sheets

Specification includes a Sequence Listing.

SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Synthetic nucleotide

<400> SEQUENCE: 1
aatgatacgg cgaccaccga                                              20

<210> SEQ ID NO 2
<211> LENGTH: 24
<212> TYPE: DNA
<213> ORGANISM: Artificial sequence
<220> FEATURE:
<223> OTHER INFORMATION: Synthetic nucleotide

<400> SEQUENCE: 2
caagcagaag acggcatacg agat                                         24

<210> SEQ ID NO 3
<211> LENGTH: 33
<212> TYPE: DNA
<213> ORGANISM: Artificial sequence
<220> FEATURE:
<223> OTHER INFORMATION: Synthetic nucleotide

<400> SEQUENCE: 3
acactctttc cctacacgac gctcttccga tct                               33

<210> SEQ ID NO 4
<211> LENGTH: 34
<212> TYPE: DNA
<213> ORGANISM: Artificial sequence
<220> FEATURE:
<223> OTHER INFORMATION: Synthetic nucleotide

<400> SEQUENCE: 4
gtgactggag ttcagacgtg tgctcttccg atct                              34

<210> SEQ ID NO 5
<211> LENGTH: 30

```
<212> TYPE: DNA
<213> ORGANISM: Artificial sequence
<220> FEATURE:
<223> OTHER INFORMATION: Synthetic nucleotide

<400> SEQUENCE: 5
ccatctcatc cctgcgtgtc tccgactcag                                          30

<210> SEQ ID NO 6
<211> LENGTH: 23
<212> TYPE: DNA
<213> ORGANISM: Artificial sequence
<220> FEATURE:
<223> OTHER INFORMATION: Synthetic nucleotide

<400> SEQUENCE: 6
cctctctatg ggcagtcggt gat                                                 23

<210> SEQ ID NO 7
<211> LENGTH: 142
<212> TYPE: PRT
<213> ORGANISM: Homo sapiens

<400> SEQUENCE: 7
```

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
    50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Leu Asn
            100                 105                 110

Phe Gln Asn Leu Ser Val Ile Gly Phe Arg Ile Leu Leu Leu Lys Val
        115                 120                 125

Ala Gly Phe Asn Leu Leu Met Thr Leu Arg Leu Trp Ser Ser
    130                 135                 140

```
<210> SEQ ID NO 8
<211> LENGTH: 429
<212> TYPE: DNA
<213> ORGANISM: Homo sapiens

<400> SEQUENCE: 8
ccaaatatcc agaaccctga ccctgccgtg taccagctga gagactctaa atccagtgac        60
aagtctgtct gcctattcac cgattttgat tctcaaacaa atgtgtcaca agtaaggat        120 tctgatgtgt atatcacaga caaaactgtg ctagacatga ggtctatgga cttcaagagc       180
aacagtgctg tggcctggag caacaaatct gactttgcat gtgcaaacgc cttcaacaac       240
agcattattc cagaagacac cttcttcccc agcccagaaa gttcctgtga tgtcaagctg       300
gtcgagaaaa gctttgaaac agatacgaac ctaaacttc aaaacctgtc agtgattggg        360
ttccgaatcc tcctcctgaa agtggccggg tttaatctgc tcatgacgct gcggctgtgg       420
tccagctga                                                              429
```

<210> SEQ ID NO 9
<211> LENGTH: 138
<212> TYPE: PRT
<213> ORGANISM: Mus musculus

<400> SEQUENCE: 9

```
Pro Tyr Ile Gln Asn Pro Glu Pro Ala Val Tyr Gln Leu Lys Asp Pro
1               5                  10                  15

Arg Ser Gln Asp Ser Thr Leu Cys Leu Phe Thr Asp Phe Asp Ser Gln
            20                  25                  30

Ile Asn Val Pro Lys Thr Met Glu Ser Gly Thr Phe Ile Thr Asp Lys
        35                  40                  45

Thr Val Leu Asp Met Lys Ala Met Asp Ser Lys Ser Asn Gly Ala Ile
    50                  55                  60

Ala Trp Ser Asn Gln Thr Ser Phe Thr Cys Gln Asp Ile Phe Lys Glu
65                  70                  75                  80

Thr Asn Ala Thr Tyr Pro Ser Ser Asp Val Pro Cys Asp Ala Thr Leu
                85                  90                  95

Thr Glu Lys Ser Phe Glu Thr Asp Met Asn Leu Asn Phe Gln Asn Leu
            100                 105                 110

Ser Val Met Gly Leu Arg Ile Leu Leu Leu Lys Val Ala Gly Phe Asn
        115                 120                 125

Leu Leu Met Thr Leu Arg Leu Trp Ser Ser
    130                 135
```

<210> SEQ ID NO 10
<211> LENGTH: 138
<212> TYPE: PRT
<213> ORGANISM: Mus musculus

<400> SEQUENCE: 10

```
Pro Asn Ile Gln Asn Pro Glu Pro Ala Val Tyr Gln Leu Lys Asp Pro
1               5                  10                  15

Arg Ser Gln Asp Ser Thr Leu Cys Leu Phe Thr Asp Phe Asp Ser Gln
            20                  25                  30

Ile Asn Val Pro Lys Thr Met Glu Ser Gly Thr Phe Ile Thr Asp Lys
        35                  40                  45

Thr Val Leu Asp Met Lys Ala Met Asp Ser Lys Ser Asn Gly Ala Ile
    50                  55                  60

Ala Trp Ser Asn Gln Thr Ser Phe Thr Cys Gln Asp Ile Phe Lys Glu
65                  70                  75                  80

Thr Asn Ala Thr Tyr Pro Ser Ser Asp Val Pro Cys Asp Ala Thr Leu
                85                  90                  95

Thr Glu Lys Ser Phe Glu Thr Asp Met Asn Leu Asn Phe Gln Asn Leu
            100                 105                 110

Ser Val Met Gly Leu Arg Ile Leu Leu Leu Lys Val Ala Gly Phe Asn
        115                 120                 125

Leu Leu Met Thr Leu Arg Leu Trp Ser Ser
    130                 135
```

<210> SEQ ID NO 11
<211> LENGTH: 414
<212> TYPE: DNA
<213> ORGANISM: Mus musculus

<400> SEQUENCE: 11

```
ccatacatcc agaacccaga acctgctgtg taccagttaa agatcctcg gtctcaggac      60 agcaccctct gcctgttcac cgactttgac tcccaaatca atgtgccgaa aaccatggaa    120
tctggaacgt tcatcactga caaaactgtg ctggacatga aagctatgga ttccaagagc    180
aatggggcca ttgcctggag caaccagaca agcttcacct gccaagatat cttcaaagag    240
accaacgcca cctaccccag ttcagacgtt ccctgtgatg ccacgttgac cgagaaaagc    300
tttgaaacag atatgaacct aaactttcaa aacctgtcag ttatgggact ccgaatcctc    360
ctgctgaaag tagcgggatt taacctgctc atgacgctga ggctgtggtc cagt          414
```

```
<210> SEQ ID NO 12
<211> LENGTH: 414
<212> TYPE: DNA
<213> ORGANISM: Mus musculus

<400> SEQUENCE: 12
```

```
ccaaacatcc agaacccaga acctgctgtg taccagttaa agatcctcg gtctcaggac      60 agcaccctct gcctgttcac cgactttgac tcccaaatca atgtgccgaa aaccatggaa    120
tctggaacgt tcatcactga caaaactgtg ctggacatga aagctatgga ttccaagagc    180
aatggggcca ttgcctggag caaccagaca agcttcacct gccaagatat cttcaaagag    240
accaacgcca cctaccccag ttcagacgtt ccctgtgatg ccacgttgac cgagaaaagc    300
tttgaaacag atatgaacct aaactttcaa aacctgtcag ttatgggact ccgaatcctc    360
ctgctgaaag tagcgggatt taacctgctc atgacgctga ggctgtggtc cagt          414
```

```
<210> SEQ ID NO 13
<211> LENGTH: 177
<212> TYPE: PRT
<213> ORGANISM: Homo sapiens

<400> SEQUENCE: 13
```

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 14
<211> LENGTH: 531
<212> TYPE: DNA
<213> ORGANISM: Homo sapiens

<400> SEQUENCE: 14

| | | | | | |
|---|---|---|---|---|---|
| gaggacctga | acaaggtgtt | cccacccgag | gtcgctgtgt | ttgagccatc | agaagcagag | 60 |
| atctcccaca | cccaaaaggc | cacactggtg | tgcctggcca | caggcttctt | ccccgaccac | 120 |
| gtggagctga | gctggtgggt | gaatgggaag | gaggtgcaca | gtggggtcag | cacagacccg | 180 |
| cagcccctca | aggagcagcc | cgccctcaat | gactccagat | actgcctgag | cagccgcctg | 240 |
| agggtctcgg | ccaccttctg | gcagaacccc | cgcaaccact | tccgctgtca | agtccagttc | 300 |
| tacgggctct | cggagaatga | cgagtggacc | caggataggg | ccaaacccgt | cacccagatc | 360 |
| gtcagcgccg | aggcctgggg | tagagcagac | tgtggcttta | cctcggtgtc | ctaccagcaa | 420 |
| ggggtcctgt | ctgccaccat | cctctatgag | atcctgctag | ggaaggccac | cctgtatgct | 480 |
| gtgctggtca | gcgcccttgt | gttgatggcc | atggtcaaga | gaaaggattt | c | 531 |

<210> SEQ ID NO 15
<211> LENGTH: 178
<212> TYPE: PRT
<213> ORGANISM: Homo sapiens

<400> SEQUENCE: 15

Asp Leu Lys Asn Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Tyr Pro Asp His Val Glu Leu Ser Trp Trp Val Asn Gly
        35                  40                  45

Lys Glu Val His Ser Gly Val Ser Thr Asp Pro Gln Pro Leu Lys Glu
    50                  55                  60

Gln Pro Ala Leu Asn Asp Ser Arg Tyr Cys Leu Ser Ser Arg Leu Arg
65                  70                  75                  80

Val Ser Ala Thr Phe Trp Gln Asn Pro Arg Asn His Phe Arg Cys Gln
                85                  90                  95

Val Gln Phe Tyr Gly Leu Ser Glu Asn Asp Glu Trp Thr Gln Asp Arg
            100                 105                 110

Ala Lys Pro Val Thr Gln Ile Val Ser Ala Glu Ala Trp Gly Arg Ala
        115                 120                 125

Asp Cys Gly Phe Thr Ser Glu Ser Tyr Gln Gln Gly Val Leu Ser Ala
    130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Ser
                165                 170                 175

Arg Gly

<210> SEQ ID NO 16
<211> LENGTH: 537
<212> TYPE: DNA
<213> ORGANISM: Homo sapiens

<400> SEQUENCE: 16

| | | | | | |
|---|---|---|---|---|---|
| gacctgaaaa | acgtgttccc | acccgaggtc | gctgtgtttg | agccatcaga | agcagagatc | 60 |

```
tcccacaccc aaaaggccac actggtatgc ctggccacag gcttctaccc cgaccacgtg      120
gagctgagct ggtgggtgaa tgggaaggag gtgcacagtg gggtcagcac agacccgcag      180
cccctcaagg agcagcccgc cctcaatgac tccagatact gcctgagcag ccgcctgagg      240
gtctcggcca ccttctggca gaaccccgc aaccacttcc gctgtcaagt ccagttctac       300
gggctctcgg agaatgacga gtggacccag gatagggcca aacccgtcac ccagatcgtc      360
agcgccgagg cctggggtag agcagactgt ggcttcacct ccgagtctta ccagcaaggg      420
gtcctgtctg ccaccatcct ctatgagatc ttgctaggga aggccacctt gtatgccgtg      480
ctggtcagtg ccctcgtgct gatggccatg gtcaagagaa aggattccag aggctag        537
```

<210> SEQ ID NO 17
<211> LENGTH: 173
<212> TYPE: PRT
<213> ORGANISM: Mus musculus

<400> SEQUENCE: 17

```
Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170
```

<210> SEQ ID NO 18
<211> LENGTH: 522
<212> TYPE: DNA
<213> ORGANISM: Mus musculus

<400> SEQUENCE: 18

```
gaggatctga gaaatgtgac tccacccaag gtctccttgt ttgagccatc aaaagcagag       60
attgcaaaca acaaaaggc taccctcgtg tgcttggcca ggggcttctt ccctgaccac       120
gtggagctga gctggtgggt gaatggcaag gaggtccaca gtggggtcag cacggaccct      180
caggcctaca aggagagcaa ttatagctac tgcctgagca gccgcctgag ggtctctgct      240
accttctggc acaatcctcg caaccacttc cgctgccaag tgcagttcca tgggctttca      300
gaggaggaca gtggccaga gggctcaccc aaacctgtca cacagaacat cagtgcagag       360
gcctggggcc gagcagactg tgggattacc tcagcatcct atcaacaagg ggtcttgtct      420
```

```
gccaccatcc tctatgagat cctgctaggg aaagccaccc tgtatgctgt gcttgtcagt    480
acactggtgg tgatggctat ggtcaaaaga aagaattcat ga                       522
```

<210> SEQ ID NO 19
<211> LENGTH: 173
<212> TYPE: PRT
<213> ORGANISM: Mus musculus

<400> SEQUENCE: 19

```
Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr His Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Gly Leu Val Leu Met Ala Met Val Lys Lys Lys Asn Ser
                165                 170
```

<210> SEQ ID NO 20
<211> LENGTH: 522
<212> TYPE: DNA
<213> ORGANISM: Mus musculus

<400> SEQUENCE: 20

```
gaggatctga aaatgtgac tccacccaag gtctccttgt ttgagccatc aaaagcagag     60
attgcaaaca acaaaaggc taccctcgtg tgcttggcca ggggcttctt ccctgaccac    120
gtggagctga gctggtgggt gaatggcaag gaggtccaca gtggggtcag cacggaccct    180
caggcctaca aggagagcaa ttatagctac tgcctgagca gccgcctgag ggtctctgct    240
accttctggc acaatcctcg aaaccacttc cgctgccaag tgcagttcca tgggctttca    300
gaggaggaca gtggccaga gggctcaccc aaacctgtca cacagaacat cagtgcagag    360
gcctggggcc gagcagactg tggaatcact tcagcatcct atcatcaggg ggttctgtct    420
gcaaccatcc tctatgagat cctactgggg aaggccaccc tatatgctgt gctggtcagt    480
ggcctggtgc tgatggccat ggtcaagaaa aaaaattcct ga                       522
```

METHODS AND COMPOSITIONS EMPLOYING BLOCKED PRIMERS

CROSS-REFERENCE TO RELATED APPLICATIONS

Pursuant to 35 U.S.C. § 119(e), this application claims priority to the filing date of the U.S. Provisional Patent Application Ser. No. 62/348,428, filed Jun. 10, 2016; the disclosure of which application is herein incorporated by reference.

INTRODUCTION

A key aspect of cellular adaptive immunity is mediated by T-cells, a class of lymphocytes with specialized extracellular receptors (T-cell receptors or TCR's). These TCR's selectively bind antigens from pathogens that have been presented by a different type of immune cell (APC's). A tremendous repertoire diversity of TCR's is required to encompass all of the specific antigen-binding possibilities. This diversity is achieved by V(D)J recombination and the resulting T-cell clonal population has a "clonotype" consisting of a particular pairing of TCR variants (TCRα and TCRβ subunits). The SMARTer Human TCR a/b Profiling Kit (Takara Bio USA Cat. Nos. 635014, 635015, 635016) is a methodology for TCR mRNA profiling. The kit utilizes a template-switching methodology (SMART; Switching Mechanism at the 5' end of RNA Template) and semi-nested PCR to reverse-transcribe and amplify variable regions of TCRα and TCRβ subunit from total RNA. The libraries are fully compatible with sequencing on Illumina's high-throughput NGS platforms. The kit is designed for used with either human peripheral blood RNA or purified human T cells. The study of T-cell repertoire diversity has research/clinical applications in aging, auto-immune diseases, cancer, stem cell transplants and vaccine development.

SUMMARY

The present disclosure provides methods, compositions, and systems employing blocked primers. Aspects of the disclosure include providing a blocked primer reaction mixture that includes a blocked primer and a template nucleic acid component from a single cell; unblocking the blocked primer to produce an active primer reaction mixture and subjecting the activated primer reaction mixture to primer extension conditions, such as nucleic acid amplification conditions.

Embodiments of the present disclosure provide methods, compositions, and systems employing blocked primer pairs that allow, for example, multiple amplification reactions in a reaction vessel (e.g., a well of a multi-well device) or container with minimal dispensing of reagents. In certain embodiments, the following reagents are employed: a) a first primer pair comprising 3'-blocked ends; b) an RNA primer, e.g., that is generally non-extendable by a thermostable DNA polymerase; and c) a second primer pair comprising 3'-blocked ends that are differentially blocked from the first primer pair. Blocking moieties that may be employed for blocked primers may vary, where examples of blocking moieties of that may be employed include thermally-labile blocking moieties, enzymatically-labile blocking moieties, light-labile blocking moieties, etc. Examples of differential blocking strategies include, but are not limited to: thermally-labile and enzymatically-labile, thermally labile and light-labile; light labile and enzymatically-labile, etc. In certain embodiments, the following reagents are employed: a) a first primer pair comprising 3'-blocked ends, e.g., that are thermo-labile (such as blocked with a thermally labile blocking moiety; b) an RNA primer, e.g., that is generally non-extendable by a thermostable DNA polymerase; c) a second primer pair comprising 3'-blocked ends that are enzyme-labile, e.g., that are blocked with an enzymatically-labile blocking moiety; and d) an enzyme capable of un-blocking said 3'-blocked ends of said second primer pair.

In some embodiments, provided herein are methods comprising: a) providing a reaction vessel (e.g., a well in a container or a multi-well plate) containing a second primer pair comprising 3'-blocked ends that are enzyme-labile (e.g., where the primer pair is in a dried or lyophilized format in the well); b) dispensing a plurality of purified RNA sequences or at least one cell (e.g., a single cell or multiple cells) to the reaction vessel, wherein the at least one cell is lysed to release a plurality of cell RNA sequences if the at least one cell is added to the reaction vessel; c) dispensing into the reaction vessel: i) a reverse-transcriptase (RT) enzyme, ii) a thermostable polymerase, iii) an RNA primer that is generally non-extendable by said thermostable polymerase (e.g., an RNA primer with at least two ribonucleotides (e.g., at least 2, 3, 4, 5 . . . 10 . . . or 20) at the 3' end)), and iv) a first primer pair comprising 3'-blocked ends that are thermo-labile; d) incubating the reaction vessel under conditions such that cDNA is synthesized from at least one of the plurality of purified or cell RNA sequences using the RNA primer and the RT enzyme; and e) thermocycling the reaction vessel under conditions such that: i) the 3'-blocked ends of the first primer pair become 3'-unblocked ends due to a temperature increase, and ii) the first primer pair and the thermostable polymerase amplify the cDNA to generate first double-stranded amplification products.

In certain embodiments, provided herein are methods comprising: a) providing a reaction vessel (e.g., a well in a container or a multi-well plate) containing a second primer pair comprising 3'-blocked ends that are enzyme-labile (e.g., where the primer pair is in a dried or lyophilized format in the well); b) dispensing a plurality of purified RNA sequences or at least one cell (e.g., a single cell or multiple cells) to the reaction vessel, wherein the at least one cell is lysed to release a plurality of cell RNA sequences if the at least one cell is added to the reaction vessel; c) dispensing into the reaction vessel: i) a reverse-transcriptase (RT) enzyme, ii) a thermostable polymerase, iii) an RNA primer that is generally non-extendable by said thermostable polymerase (e.g., an RNA primer with at least two ribonucleotides (e.g., at least 2, 3, 4, 5 . . . 10 . . . or 20) at the 3' end)), and iv) a first primer pair comprising 3'-blocked ends that are thermo-labile; d) incubating the reaction vessel under conditions such that cDNA is synthesized from at least one of the plurality of purified or cell RNA sequences using the RNA primer and the RT enzyme; e) thermocycling the reaction vessel under conditions such that: i) the 3'-blocked ends of the first primer pair become 3'-unblocked ends due to a temperature increase, and ii) the first primer pair and the thermostable polymerase amplify the cDNA to generate first double-stranded amplification products; f) dispensing an enzyme to the reaction vessel such that the enzyme causes the 3'-blocked ends of the second primer pair to become 3'-unblocked ends; and g) thermocycling the reaction vessel under conditions such that the first double-stranded products (e.g., PCR products) are amplified using the second primer pair to generate second double-stranded products (e.g., PCR products).

In other embodiments, provided herein are systems or compositions comprising: a) a first primer pair comprising 3'-blocked ends that are thermo-labile; b) an RNA primer that is generally non-extendable by a thermostable polymerase, such as Taq (e.g., an RNA primer with at least two ribonucleotides at the 3' end), c) a second primer pair comprising 3'-blocked ends that are enzyme-labile; and d) an enzyme capable of un-blocking the 3'-blocked ends of the second primer pair. In certain embodiments, the systems and compositions further comprise: e) a plurality of purified RNA sequences and/or at least one isolated cell (e.g., a T-cell or other cell). In further embodiments, the methods further comprise a multi-well device and/or a thermocycler and/or a robotic dispensing system and/or a nucleic acid sequencing device.

In certain embodiments, provided herein are methods comprising: a) providing a reaction vessel containing a first primer pair comprising 3'-blocked ends that are enzyme-labile; b) dispensing a plurality of purified RNA sequences or at least one cell to said well, wherein said at least one cell is lysed to release a plurality of cell RNA sequences if said at least one cell is added to said well; c) dispensing into said reaction vessel: i) a reverse-transcriptase (RT) enzyme that adds a plurality of non-templated nucleotides during cDNA synthesis, ii) a thermostable polymerase, iii) an RNA primer that is generally non-extendable by the thermostable polymerase, and iv) a template switching oligonucleotide that is able to hybridize to said non-templated nucleotides and which includes a plurality of isoC and/or isoG nucleotides; d) incubating said reaction vessel under conditions such that: i) said cDNA is synthesized from at least one of said plurality of purified or cell RNA sequences using said RNA primer and said RT enzyme, wherein said cDNA includes said plurality of non-templated nucleotides, and ii) said template switching oligonucleotide hybridizes to said non-templates nucleotides such that it is incorporated into said cDNA; e) dispensing an enzyme into said reaction vessel such that said enzyme causes said 3'-blocked ends of said first primer pair to become 3'-unblocked ends; and f) thermocycling said reaction vessel under conditions such that said first primer pair and said thermostable polymerase amplify said cDNA to generate first double-stranded amplification products.

In certain embodiments, provided herein are systems and compositions comprising: a) a first primer pair comprising 3'-blocked ends that are enzyme-labile; b) an RNA primer with at least two ribonucleotides at the 3' end, c) a template switching oligonucleotide comprising a plurality of isoC and/or isoG nucleotides; and d) an enzyme capable of un-blocking said 3'-blocked ends of said first primer pair. In certain embodiments, the compositions and systems further comprise: e) a reverse-transcriptase (RT) enzyme that adds a plurality of non-templated nucleotides during cDNA synthesis, wherein said template switching oligonucleotide is able to hybridize to said non-templated nucleotides.

In some embodiments, the reaction vessel is a well that is part of a multi-well device comprising a plurality of wells. In other embodiments, the plurality of wells all have a second primer pair comprising 3' blocked ends that are enzyme-labile, and wherein steps b) through g) are conducted in all of the plurality of wells. In other embodiments, the enzyme in step f) comprises a T4 poly-nucleotide kinase. In particular embodiments, a plurality of purified RNA sequences are dispensed in step b). In additional embodiments, the at least one cell is dispensed in step b), and cell well is treated such that the at least one cell is lysed releasing the plurality of cell RNA.

In certain embodiments, the RT enzyme adds a plurality of non-templated nucleotides (e.g., a stretch of C's) upon reaching the 5' end of each mRNA template when the cDNA is synthesized. In other embodiments, the dispensing in step c) further includes v) a template switching oligonucleotide (e.g., comprising a stretch of G's) that hybridizes to the non-templated nucleotides such that it is incorporated into the cDNA.

In some embodiments, the first primer pair comprises a first primer and a second primer, and wherein the first primer hybridizes to the template switching oligonucleotide that is part of the cDNA during the PCR amplifying in step e). In other embodiments, the first primer comprises a well-specific barcode sequence, and the second primer comprises a UMI molecule specific sequence. In other embodiments, the second primer pair comprises a third primer and a fourth primer, wherein the third primer comprises a first plate-specific sequence and a first sequencing adaptor sequence, and the fourth primer comprises a second plate-specific sequence a second sequencing adaptor sequence.

In certain embodiments, the thermostable polymerase comprises Taq polymerase. In other embodiments, the thermostable polymerase is unable to extend the RNA primer. In additional embodiments, the dispensing in step f) further comprises adding additional thermostable polymerase. In other embodiments, the RNA primer comprises at least 3 ribonucleotides at the 3' end. In additional embodiments, the first primer pair comprises a first primer and a second primer, wherein the second primer hybridizes to a constant region of a T-cell receptor (TCR). In some embodiments, the plurality of purified or cell RNA sequences are from a T-cell. In certain embodiments, the methods further comprise: h) sequencing the second-double stranded PCR products. In other embodiments, the sequencing reveals the T-cell receptor variant diversity from the at least one cell.

In some embodiments, the reaction vessel is a well that is part of a multi-well device. In certain embodiments, the multi-well device comprises at least 50 wells (e.g., 50 . . . 100 . . . 150 . . . 400 . . . 689 . . . 900 . . . or more). In additional embodiments, the multi-well device comprises at least 1000 wells (e.g., 1000 . . . 1500 . . . 2500 . . . 5000 . . . 5184 . . . 10,000 . . . 20,000 . . . or more). In other embodiments, the multi-well device comprises a multi-well chip. In other embodiments, the dispensing volume is between 25 and 500 nl, or between 50 nl and 1 µl.

DEFINITIONS

Figure 1:
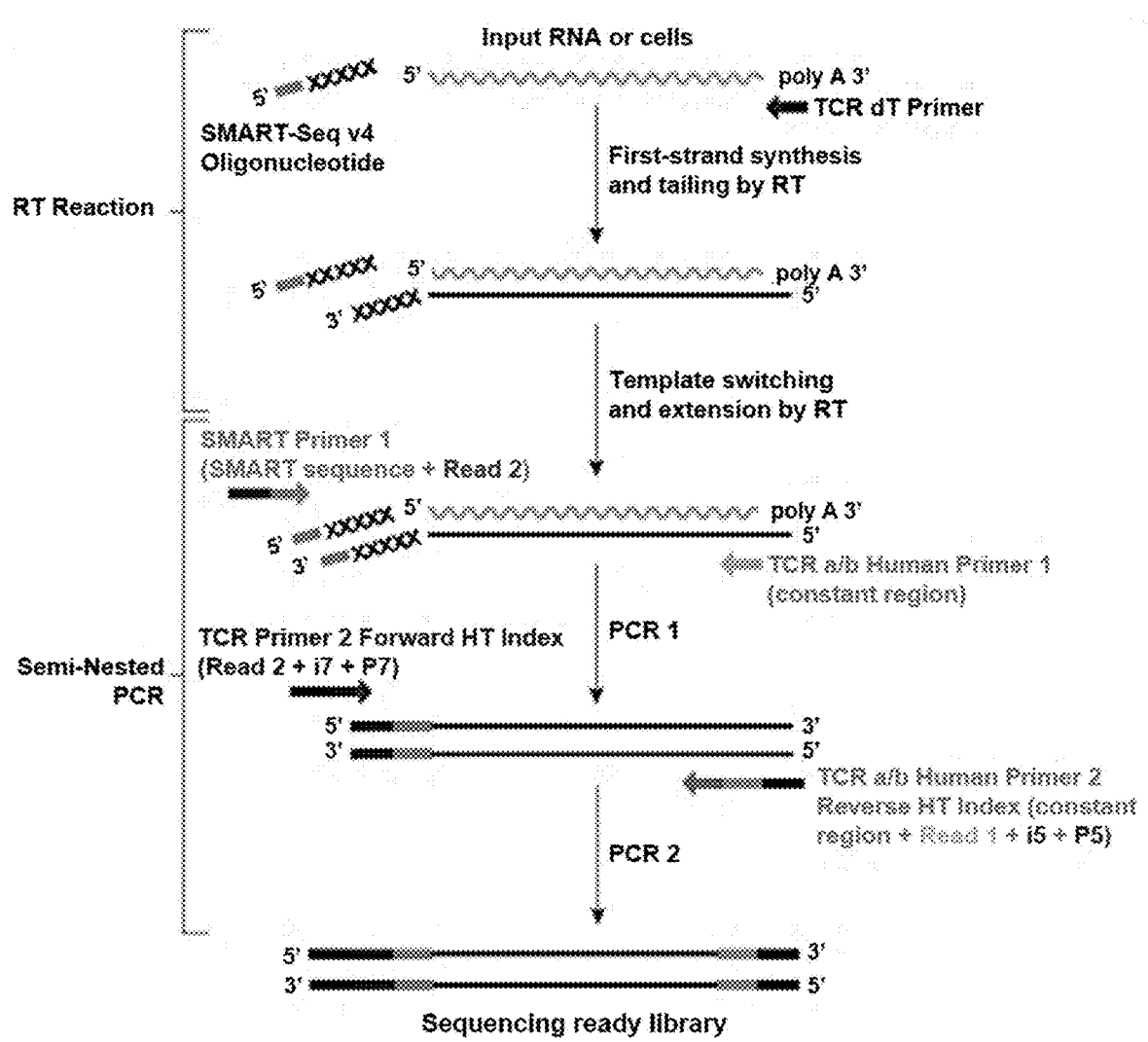
FIG. 1 shows a schematic of the technology and workflow for the SMARTer Human TCR a/b profiling kit and method from Takara Bio USA (Mountain View, Calif.).

As used herein, the term "hybridization conditions" means conditions in which a primer, or other polynucleotide, specifically hybridizes to a region of a target nucleic acid with which the primer or other polynucleotide shares some complementarity. Whether a primer specifically hybridizes to a target nucleic acid is determined by such factors as the degree of complementarity between the polymer and the target nucleic acid and the temperature at which the hybridization occurs, which may be informed by the melting temperature ($T_M$) of the primer. The melting temperature refers to the temperature at which half of the primer-target nucleic acid duplexes remain hybridized and half of the duplexes dissociate into single strands. The Tm of a duplex may be experimentally determined or predicted using the following formula Tm=81.5+16.6(log 10[Na+])+0.41 (fraction G+C)−(60/N), where N is the chain length and [Na+] is less than 1 M. See Sambrook and Russell (2001; Molecular Cloning: A Laboratory Manual, 3rd ed., Cold Spring Harbor Press, Cold Spring Harbor N.Y., Ch. 10). Other more advanced models that depend on various parameters may also be used to predict Tm of primer/target duplexes depending on various hybridization conditions. Approaches for achieving specific nucleic acid hybridization may be found in, e.g., Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993).

The terms "complementary" and "complementarity" as used herein refer to a nucleotide sequence that base-pairs by non-covalent bonds to all or a region of a target nucleic acid (e.g., a region of the product nucleic acid). In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotides are complementary to every nucleotide in the target nucleic acid in all the corresponding positions. For example, a primer may be perfectly (i.e., 100%) complementary to the target nucleic acid, or the primer and the target nucleic acid may share some degree of complementarity which is less than perfect (e.g., 70%, 75%, 85%, 90%, 95%, 99%).

The percent identity of two nucleotide sequences can be determined by aligning the sequences for optimal comparison purposes (e.g., gaps can be introduced in the sequence of a first sequence for optimal alignment). The nucleotides at corresponding positions are then compared, and the percent identity between the two sequences is a function of the number of identical positions shared by the sequences (i.e., % identity=# of identical positions/total # of positions× 100). When a position in one sequence is occupied by the same nucleotide as the corresponding position in the other sequence, then the molecules are identical at that position. A non-limiting example of such a mathematical algorithm is described in Karlin et al., Proc. Natl. Acad. Sci. USA 90:5873-5877 (1993). Such an algorithm is incorporated into the NBLAST and XBLAST programs (version 2.0) as described in Altschul et al., Nucleic Acids Res. 25:389-3402 (1997). When utilizing BLAST and Gapped BLAST programs, the default parameters of the respective programs (e.g., NBLAST) can be used. In one aspect, parameters for sequence comparison can be set at score=100, wordlength=12, or can be varied (e.g., wordlength=5 or wordlength=20).

A domain refers to a stretch or length of a nucleic acid made up of a plurality of nucleotides, where the stretch or length provides a defined function to the nucleic acid. Examples of domains include primer binding domains, hybridization domains, barcode domains (such as source barcode domains), unique molecular identifier (UMI) domains, Next Generation Sequencing (NGS) adaptor domains, NGS indexing domains, etc. In some instances, the terms "domain" and "region" may be used interchangeably, including e.g., where immune receptor chain domains/regions are described, such as e.g., immune receptor constant domains/regions. While the length of a given domain may vary, in some instances the length ranges from 2 to 100 nt, such as 5 to 50 nt, e.g., 5 to 30 nt.

DETAILED DESCRIPTION

The present disclosure provides methods, compositions, and systems employing blocked primers. Aspects of the disclosure include providing a blocked primer reaction mixture that includes a blocked primer and a template nucleic acid component from a single cell; unblocking the blocked primer to produce an active primer reaction mixture and subjecting the activated primer reaction mixture to primer extension conditions, such as nucleic acid amplification conditions.

Embodiments of the present disclosure provides methods, compositions, and systems employing blocked primer pairs that allow, for example, multiple amplification reactions in a reaction vessel (e.g., a well of a multi-well device) or container with minimal dispensing of reagents. In some embodiments, two pairs of differentially blocked primers are employed. In certain embodiments, the following reagents are employed: a) a first primer pair comprising 3'-blocked ends that are thermo-labile; b) an RNA primer that is generally non-extendable by a thermostable DNA polymerase; c) a second primer pair comprising 3'-blocked ends that are enzyme-labile; and d) an enzyme capable of unblocking said 3'-blocked ends of said second primer pair.

Before the methods of the present disclosure are described in greater detail, it is to be understood that the methods are not limited to particular embodiments described, as such may, of course, vary. It is also to be understood that the terminology used herein is for the purpose of describing particular embodiments only, and is not intended to be limiting, since the scope of the methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods. The upper and lower limits of these smaller ranges may independently be included in the smaller ranges and are also encompassed within the methods, subject to any specifically excluded limit in the stated range. Where the stated range includes one or both of the limits, ranges excluding either or both of those included limits are also included in the methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods belong. Although any methods similar or equivalent to those described herein can also be used in the practice or testing of the methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present methods are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, which are, for clarity, described in the context of separate embodiments, may also be provided in combination in a single embodiment. Conversely, various features of the methods, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order which is logically possible.

A. Overview

As summarized above, aspects of the invention include employing blocked primers in primer extension reactions, e.g., nucleic acid amplification reactions, where the template is a nucleic acid of a template nucleic acid component. In a given protocol, a single blocked primer may be employed or a pair of blocked primers may be employed. The term "blocked primer" refers to a primer nucleic acid that includes a blocking moiety, which blocking moiety renders the primer incapable of serving as a primer in a template mediate primer extension reaction. Removal of the blocking moiety from a blocked primer produces an unblocked primer, which unblocked primer is capable of acting as a primer in a template mediated primer extension reaction. Any convenient blocking moiety may be employed in a given blocked primer, where blocking moieties of interest include, but are not limited to: thermally-labile blocking moieties, enzymatically-labile blocking moieties, light-labile blocking moieties, and the like.

In some instances, the blocking moiety is a thermally-labile blocking moiety. A thermally-labile blocking moiety is a moiety that may be removed from a primer when the temperature of the primer is raised above a certain threshold value. While the threshold value may vary, in some instances the threshold value is 60° C. or higher, such as 75° C. or higher, including 90° C. or higher. Examples of thermally labile moieties that may be employed to block primers in accordance with the invention include, but are not limited to, those described in U.S. Pat. Nos. 8,133,669 and 8,361,753; the disclosures of which are herein incorporated by reference. In some instances, the thermally labile blocking moiety is a 3' blocking moiety, such as but not limited to: O-phenoxyacetyl; O-methoxyacetyl; O-acetyl; O-(p-toluene)sulfonate; O-phosphate; O-nitrate; O-[4-methoxy]-tetrahydrothiopyranyl; O-tetrahydrothiopyranyl; O-[5-methyl]-tetrahydrofuranyl; O-[2-methyl,4-methoxy]-tetrahydropyranyl; O-[5-methyl]-tetrahydropyranyl; and O-tetrahydrothiofuranyl.

In some instances, the blocking moiety is an enzymatically-labile blocking moiety. An enzymatically-labile blocking moiety is a moiety that may be removed from a primer by exposing the primer to a suitable enzyme that cleaves the moiety from the primer to produce an unblocked primer. Examples of enzymatically-labile blocking moieties of interest include those having a polymerase activity blocking group attached to the blocked primer, e.g., to the 3' end of the blocked primer, through a linkage group cleavable by a hydrolase enzyme. Examples of hydrolase enzymes of interest include, but are not limited to: esterases, phosphatases, peptidases, penicillin amidases, glycosidases and phosphorylases, kinases, etc. Polymerase blocking groups, hydrolase susceptible linkages and hydrolase enzymes are further described in U.S. Patent Application Publication No. 20050164182 and U.S. Pat. No. 7,078,499; the disclosures of which are herein incorporated by reference.

In some instances, the blocking moiety is a chemically-labile blocking moiety. A chemically-labile blocking moiety is a moiety that may be removed from a primer by exposing the primer to a chemical agent that removes the moiety from the primer to produce an unblocked primer. The chemically-labile blocking moiety may be reactive with the functional group of a chemical agent (e.g., an azido-containing modifiable group that is reactive with an alkynyl-containing reagent or a phosphine reagent, or vice versa, or a disulfide that is reactive with a reducing agent such as tris(2-carboxyethyl)phosphine (TCEP) or DTT). A variety of functional group chemistries and chemical agent stimuli suitable for modifying them may be utilized in the subject methods. Functional group chemistries and chemical agents of interest include, but are not limited to, Click chemistry groups and reagents (e.g., as described by Sharpless et al., (2001), "Click Chemistry: Diverse Chemical Function from a Few Good Reactions", Angewandte Chemie International Edition 40 (11): 2004-2021), Staudinger ligation groups and reagents (e.g., as described by Bertozzi et al., (2000), "Cell Surface Engineering by a Modified Staudinger Reaction", Science 287 (5460): 2007), and other bioconjugation groups and reagents (e.g., as described by Hermanson, Bioconjugate Techniques, Second Edition, Academic Press, 2008). In certain embodiments, the chemically-labile blocking moiety includes a functional group selected from an azido, a phosphine (e.g., a triaryl phosphine or a trialkyl phosphine or mixtures thereof), a dithiol, an active ester, an alkynyl, a protected amino, a protected hydroxy, a protected thiol, a hydrazine, and a disulfide.

In some instances, the blocking moiety is a light-labile blocking moiety. A light-labile blocking moiety is a moiety that may be removed from a primer by exposing the primer to light at a wavelength that cleaves the moiety from the primer to produce an unblocked primer. Examples of light-labile blocking moieties of interest include those having a polymerase activity blocking group attached to the blocked primer, e.g., to the 3' end of the blocked primer, through a linkage group cleavable by light of a certain wavelength that cleaves a photocleavable group in the linkage group. Any convenient photocleavable groups may find use. Cleavable groups and linkers may include photocleavable groups comprising covalent bonds that break upon exposure to light of a certain wavelength. Suitable photocleavable groups and linkers for use in the subject MCIPs include ortho-nitrobenzyl-based linkers, phenacyl linkers, alkoxybenzoin linkers, chromium arene complex linkers, NpSSMpact linkers and pivaloylglycol linkers, as described in Guillier et al. (Chem. Rev. 2000 1000:2091-2157). For example, a 1-(2-nitrophenyl)ethyl-based photocleavable linker (Ambergen) can be efficiently cleaved using near-UV light, e.g., in >90% yield in 5-10 minutes using a 365 nm peak lamp at 1-5 mW/cm2. In some embodiments, the modifiable group is a photocleavable group such as a nitro-aryl group, e.g., a nitro-indole group or a nitro-benzyl group, including but not limited to: 2-nitroveratryloxycarbonyl, α-carboxy-2-nitrobenzyl, 1-(2-nitrophenyl)ethyl, 1-(4,5-dimethoxy-2-nitrophenyl)ethyl and 5-carboxymethoxy-2-nitrobenzyl. Nitro-indole groups of interest include, e.g., a 3-nitro-indole, a 4-nitro indole, a 5-nitro indole, a 6-nitro-indole or a 7-nitro-indole group, where the indole ring may be further substituted at any suitable position, e.g., with a methyl group or a halo group (e.g., a bromo or chloro), e.g., at the 3-, 5- or 7-position. In certain embodiments, the nitro-aryl group is a 7-nitro indolyl group. In certain instances, the 7-nitro indolyl group is further substituted with a substituent that increases the photoactivity of the group, e.g., substituted with a bromo at the 5-position. Any convenient photochemistry of nitroaryl groups may be adapted for use in the subject MCIPs to provide a suitable modifiable group. In certain embodiments, the MCIP includes a linker that includes a photocleavable group, such as a nitro-benzyl protecting group or a nitro-indolyl group. In certain embodiments, the modifiable group is of the structure: —$NZ_1Z_2$ where $Z_1$ is H or a $C_1$-$C_8$ alkyl residue, and $Z_2$ is a photocleavable group such as a nitro-aryl group.

In some instances, a workflow of embodiments of the invention includes use of multiple pairs of differentially blocked primers, e.g., two pairs of differentially blocked primers, i.e., a first pair of blocked primers and a second pair of blocked primers that is differentially blocked from the first pair of blocked primers. As the primers of the multiple pairs are differentially blocked, the blocking moieties of one given pair are removed using a different stimulus than the blocking moieties of another given pair. For example, a first given pair of primers may be blocked with thermally labile blocking moieties, while a second given pair may be blocked with enzymatically labile blocking moieties. Differentially labile blocking moieties of interest include, but are not limited to thermally-labile blocking moieties and enzymatically-labile blocking moieties, thermally-labile blocking moieties and light-labile blocking moieties, light-labile blocking moieties and enzymatically-labile blocking moieties; and the like.

As summarized above, aspects of embodiments of the methods include providing a blocked primer reaction mixture that includes: a pair of blocked amplification primers, e.g., as described above; and a template nucleic acid component. Template nucleic acid components are nucleic acid samples that contain one or more types of template nucleic acids, as described in more detail below. Template nucleic acid components may be derived from cellular samples including cellular samples that contain a single cell or a population of cells containing, e.g., two or more cells. Cellular samples may be derived from a variety of sources including but not limited to e.g., a cellular tissue, a biopsy, a blood sample, a cell culture, etc. Additionally, cellular samples may be derived from specific organs, tissues, tumors, neoplasms, or the like. Furthermore, cells from any population can be the source of a cellular sample used in the subject methods, such as a population of prokaryotic or eukaryotic single celled organisms including bacteria or yeast. However, where the instant methods include preparing an immune cell receptor repertoire library, eukaryotic cells including mammalian cells will generally be employed as the source of the RNA sample.

As such, in some instances, the source of an RNA sample utilized in the subject methods may be a mammalian cellular sample, such as a rodent (e.g., mouse or rat) cellular sample, a non-human primate cellular sample, a human cellular sample, or the like. In some instances, a mammalian cellular sample may be mammalian blood sample, including but not limited to e.g., a rodent (e.g., mouse or rat) blood sample, a non-human primate blood sample, a human blood sample, or the like.

In some embodiments, useful cellular samples may include those that contain one or more immune cell types. As used herein, the term "immune cells" generally includes white blood cells (leukocytes) which are derived from hematopoietic stem cells (HSC) produced in the bone marrow. "Immune cells" includes, e.g., lymphocytes (T cells, B cells, natural killer (NK) cells) and myeloid-derived cells (neutrophil, eosinophil, basophil, monocyte, macrophage, dendritic cells). "T cell" includes all types of immune cells expressing CD3 including T-helper cells (CD4+ cells), cytotoxic T-cells (CD8+ cells), T-regulatory cells (Treg) and gamma-delta T cells. A "cytotoxic cell" includes CD8+ T cells, natural-killer (NK) cells, and neutrophils, which cells are capable of mediating cytotoxicity responses.

In some instances, a RNA sample used in a method described herein will be derived from a population of immune cells, including but not limited to e.g., a mixed population of immune cells, a population of T cells, a population of B cells, or the like. In some instances, a RNA sample used in a method described herein will be derived from a single immune cell, including but not limited to e.g., a single T cell, a single B cell, or the like.

In some instances the template nucleic acid component is from a single cell. A template nucleic acid component from a single cell is a nucleic acid composition, e.g., a composition of one or more distinct nucleic acids, such as ribonucleic acids or deoxyribonucleic acids, that originate or are derived from a single cell. As used herein, a "single cell" refers to one cell. Single cells useful as the source of template nucleic acids, e.g., RNAs or DNAs, can be obtained from a tissue of interest, or from a biopsy, blood sample, or cell culture, etc. Additionally, cells from specific organs, tissues, tumors, neoplasms, or the like can be obtained and used in the methods described herein.

Single cells, for use in such methods, may be obtained by any convenient method. For example, in some instances, single cells may be obtained through limiting dilution of cellular sample. In some instances, the present methods may include a step of obtaining single cells. A single cell suspension can be obtained using standard methods known in the art including, for example, enzymatically using trypsin or papain to digest proteins connecting cells in tissue samples or releasing adherent cells in culture, or mechanically separating cells in a sample. Single cells can be placed in any suitable reaction vessel in which single cells can be treated individually. For example a 96-well plate, 384 well plate, or a plate with any number of wells such as 2000, 4000, 6000, or 10000 or more. The multi-well plate can be part of a chip and/or device. The present disclosure is not limited by the number of wells in the multi-well plate. In various embodiments, the total number of wells on the plate is from 100 to 200,000, or from 5000 to 10,000. In other embodiments the plate comprises smaller chips, each of which includes 5,000 to 20,000 wells. For example, a square chip may include 125 by 125 nanowells, with a diameter of 0.1 mm. Such methods are further described in greater detail below.

In some instances, single cells may be obtained by sorting a cellular sample using a cell sorter instrument. By "cell sorter" as used herein is meant any instrument that allows for the sorting of individual cells into an appropriate vessel for downstream processes, such as those processes of library preparation as described herein. Useful cell sorters include flow cytometers, such as those instruments utilized in fluorescence activated cell sorting (FACS). Flow cytometry is a well-known methodology using multi-parameter data for identifying and distinguishing between different particle (e.g., cell) types i.e., particles that vary from one another terms of label (wavelength, intensity), size, etc., in a fluid medium. In flow cytometrically analyzing a sample, an aliquot of the sample is first introduced into the flow path of the flow cytometer. When in the flow path, the cells in the sample are passed substantially one at a time through one or more sensing regions, where each of the cells is exposed separately individually to a source of light at a single wavelength (or in some instances two or more distinct sources of light) and measurements of scatter and/or fluorescent parameters, as desired, are separately recorded for each cell. The data recorded for each cell is analyzed in real time or stored in a data storage and analysis means, such as a computer, for later analysis, as desired.

Cells sorted using a flow cytometer may be sorted into a common vessel (i.e., a single tube), or may be separately sorted into individual vessels. For example, in some instances, cells may be sorted into individual wells of a multi-well plate, as described below.

According to certain embodiments, cell sorting may include upstream processes of cell analysis and/or identification, also sometimes referred to as phenotyping. For example, in some instances, cells of a cellular sample may be identified by FACS sorting as having a particular phenotypic characteristic (surface marker expression, viability, morphology, gene expression, cytokine expression, etc.) and selected for further processing based on the characteristic. For example, in some instances, cells of a cellular sample may be sorted based on expressing one or more immune cell markers including e.g., a T cell marker, a B cell marker, or the like, and collected for further downstream processes. In one example, T cells may be selected based on the expression of one or more T cell surface markers (e.g., CD4, CD8, etc.) and the T cells may be collected for further processing. In some instances, cells collected (e.g., through FACS sorting) may be redistributed into single cell samples prior to further processing, including library preparation, as described herein.

Useful cell sorters also include multi-well-based systems that do not employ flow cytometry. Such multi-well based systems include essentially any system where cells may be deposited into individual wells of a multi-well container by any convenient means, including e.g., through the use of Poisson distribution (i.e., limiting dilution) statistics, individual placement of cells (e.g., through manual cell picking or dispensing using a robotic arm or pipettor). In some instances, useful multi-well systems include a multi-well wafer or chip, where cells are deposited into the wells or the wafer/chip and individually identified by a microscopic analysis system. In some instances, an automated microscopic analysis system may be employed in conjunction with a multi-well wafer/chip to automatically identify individual cells to be subjected to downstream analyses, including library preparation, as described herein.

In some instances, one or more cells may be sorted into or otherwise transferred to an appropriate reaction vessel. Reaction components may be added to reaction vessels, including e.g., components for preparing an template nucleic acid component, components for generating a product double stranded cDNA, components for one or more library preparation reactions, etc. Reaction vessels into which the reaction mixtures and components thereof may be added and within which the reactions of the subject methods may take place will vary. Useful reaction vessels include but are not limited to e.g., tubes (e.g., single tubes, multi-tube strips, etc.), wells (e.g., of a multi-well plate (e.g., a 96-well plate, 384 well plate, or a plate with any number of wells such as 2000, 4000, 6000, or 10000 or more). Multi-well plates may be independent or may be part of a chip and/or device, e.g., as described in greater detail below.

In some instances, reaction mixtures and components thereof may be added to and the reactions of the subject methods may take place in a liquid droplet (e.g., a water-oil emulsion droplet), e.g., as described in more detail below. Whereas the droplets may serve the purpose of individual reaction vessels, the droplets (or emulsion containing droplets) will generally be housed in a suitable container such as, e.g., a tube or well or microfluidic channel. Amplification reactions performed in droplets may be sorted, e.g., based on fluorescence (e.g., from nucleic acid detection reagent or labeled probe), using a fluorescence based droplet sorter.

Useful fluorescence based droplet sorters will vary and may include e.g., a flow cytometers, microfluidic-based droplet sorters, and the like.

In certain embodiments of the methods described herein, droplets are obtained and a single droplet is sorted into one well of a multi-well plate, or other suitable container, such as a microfluidic chamber or tube. The reaction mixture may be added directly to the droplet, e.g., without additional purification.

In some instances, the methods may include the step of obtaining single droplets. Obtaining droplets cells may be done according to any convenient protocol, including e.g., mechanically sorting droplets (e.g., utilizing a fluorescence based sorter (e.g., a flow cytometer or microfluidic-based sorter). Single droplets can be placed in any suitable reaction vessel in which single droplets can be treated individually. For example a 96-well plate, 384 well plate, or a plate with any number of wells such as 2000, 4000, 6000, or 10000 or more. The multi-well plate can be part of a chip and/or device. The present disclosure is not limited by the number of wells in the multi-well plate. In various embodiments, the total number of wells on the plate is from 100 to 200,000, or from 5000 to 10,000. In other embodiments the plate comprises smaller chips, each of which includes 5,000 to 20,000 wells. For example, a square chip may include 125 by 125 nanowells, with a diameter of 0.1 mm.

The wells (e.g., nanowells) in the multi-well plates may be fabricated in any convenient size, shape or volume. The well may be 100 µm to 1 mm in length, 100 µm to 1 mm in width, and 100 µm to 1 mm in depth. In various embodiments, each nanowell has an aspect ratio (ratio of depth to width) of from 1 to 4. In one embodiment, each nanowell has an aspect ratio of 2. The transverse sectional area may be circular, elliptical, oval, conical, rectangular, triangular, polyhedral, or in any other shape. The transverse area at any given depth of the well may also vary in size and shape.

In certain embodiments, the wells have a volume of from 0.1 nl to 1 µl. The nanowell may have a volume of 1 µl or less, such as 500 nl or less. The volume may be 200 nl or less, such as 100 nl or less. In an embodiment, the volume of the nanowell is 100 nl. Where desired, the nanowell can be fabricated to increase the surface area to volume ratio, thereby facilitating heat transfer through the unit, which can reduce the ramp time of a thermal cycle. The cavity of each well (e.g., nanowell) may take a variety of configurations. For instance, the cavity within a well may be divided by linear or curved walls to form separate but adjacent compartments, or by circular walls to form inner and outer annular compartments.

The wells can be designed such that a single well includes a single cell or a single droplet. An individual cell or droplet may also be isolated in any other suitable container, e.g., microfluidic chamber, droplet, nanowell, tube, etc. Any convenient method for manipulating single cells or droplets may be employed, where such methods include fluorescence activated cell sorting (FACS), robotic device injection, gravity flow, or micromanipulation and the use of semi-automated cell pickers (e.g. the Quixell™ cell transfer system from Stoelting Co.), etc. In some instances, single cells or droplets can be deposited in wells of a plate according to Poisson statistics (e.g., such that approximately 10%, 20%, 30% or 40% or more of the wells contain a single cell or droplet—which number can be defined by adjusting the number of cells or droplets in a given unit volume of fluid that is to be dispensed into the containers). In some instances, a suitable reaction vessel comprises a droplet (e.g., a microdroplet). Individual cells or droplets can, for example, be individually selected based on features detectable by microscopic observation, such as location, morphology, the presence of a reporter gene (e.g., expression), the presence of a bound antibody (e.g., antibody labelling), FISH, the presence of an RNA (e.g., intracellular RNA labelling), or qPCR.

Following obtainment of a desired cell population or single cells, e.g., as described above, nucleic acids can be released from the cells by lysing the cells. Lysis can be achieved by, for example, heating or freeze-thaw of the cells, or by the use of detergents or other chemical methods, or by a combination of these. However, any suitable lysis method can be used. In some instances, a mild lysis procedure can advantageously be used to prevent the release of nuclear chromatin, thereby avoiding genomic contamination of a cDNA library, and to minimize degradation of mRNA. For example, heating the cells at 72° C. for 2 minutes in the presence of Tween-20 is sufficient to lyse the cells while resulting in no detectable genomic contamination from nuclear chromatin. Alternatively, cells can be heated to 65° C. for 10 minutes in water (Esumi et al., Neurosci Res 60(4):439-51 (2008)); or 70° C. for 90 seconds in PCR buffer II (Applied Biosystems) supplemented with 0.5% NP-40 (Kurimoto et al., Nucleic Acids Res 34(5):e42 (2006)); or lysis can be achieved with a protease such as Proteinase K or by the use of chaotropic salts such as guanidine isothiocyanate (U.S. Publication No. 2007/0281313).

In some instances, the template nucleic acid component is obtained from a portion of a single cell. Single cell portions of interest include, but are not limited to: organelles, exosomes or more broadly nucleic acids contained within, or associated with, a protein and or lipid bearing membrane.

Template nucleic acids of template nucleic acid components employed in embodiments of the invention may contain a plurality of distinct template nucleic acids of differing sequence. Template nucleic acids (e.g., a template RNA, a template DNA, or the like) may be polymers of any length. While the length of the polymers may vary, in some instances the polymers are 10 nts or longer, 20 nts or longer, 50 nts or longer, 100 nts or longer, 500 nts or longer, 1000 nts or longer, 2000 nts or longer, 3000 nts or longer, 4000 nts or longer, 5000 nts or longer or more nts. In certain aspects, template nucleic acids are polymers, where the number of bases on a polymer may vary, and in some instances is 10 nts or less, 20 nts or less, 50 nts or less, 100 nts or less, 500 nts or less, 1000 nts or less, 2000 nts or less, 3000 nts or less, 4000 nts or less, or 5000 nts or less, 10,000 nts or less, 25,000 nts or less, 50,000 nts or less, 75,000 nts or less, 100,000 nts or less.

According to certain embodiments, the template nucleic acids are template ribonucleic acids (template RNA). Template RNAs may be any type of RNA (or sub-type thereof) including, but not limited to, a messenger RNA (mRNA), a microRNA (miRNA), a small interfering RNA (siRNA), a transacting small interfering RNA (ta-siRNA), a natural small interfering RNA (nat-siRNA), a ribosomal RNA (rRNA), a transfer RNA (tRNA), a small nucleolar RNA (snoRNA), a small nuclear RNA (snRNA), a long non-coding RNA (lncRNA), a non-coding RNA (ncRNA), a transfer-messenger RNA (tmRNA), a precursor messenger RNA (pre-mRNA), a small Cajal body-specific RNA (scaRNA), a piwi-interacting RNA (piRNA), an endoribonuclease-prepared siRNA (esiRNA), a small temporal RNA (stRNA), a signal recognition RNA, a telomere RNA, a ribozyme, or any combination of RNA types thereof or subtypes thereof.

According to certain embodiments, the template nucleic acids are template deoxyribonucleic acids (template DNA). A template DNA may be any type of DNA of interest to a practitioner of the subject methods, including but not limited to genomic DNA or fragments thereof, complementary DNA (or "cDNA", synthesized from any RNA or DNA of interest), recombinant DNA (e.g., plasmid DNA), or the like.

The number of distinct template nucleic acids of differing sequence in a given template nucleic acid composition may vary. While the number of distinct template nucleic acids in a given template nucleic acid composition may vary, in some instances the number of distinct template nucleic acids in a given template nucleic acid composition ranges from 1 to $10^8$, such as 1 to $10^7$, including 1 to $10^5$.

The template nucleic acid composition employed in such methods may be any suitable nucleic acid sample. The nucleic acid sample that includes the template nucleic acid may be combined into the reaction mixture in an amount sufficient for producing the product nucleic acid. According to one embodiment, the nucleic acid sample is combined into the reaction mixture such that the final concentration of nucleic acid in the reaction mixture is from 1 fg/μL to 10 μg/μL, such as from 1 pg/μL to 5 μg/μL, such as from 0.001 μg/μL to 2.5 μg/μL, such as from 0.005 μg/μL to 1 μg/μL, such as from 0.01 μg/μL to 0.5 μg/μL, including from 0.1 μg/μL to 0.25 μg/μL.

In embodiments of the methods, following preparation of a blocked primer reaction mixture, e.g., as described above, the blocked primers are unblocked in order to produce an activated primer reaction mixture. Unblocking of the blocked primers may vary, e.g., depending on the nature of the blocking moieties of the blocked primers. Where the blocked primers are blocked with thermally-labile blocking moieties, unblocking may include heating the blocked primer reaction mixture above a threshold temperature, e.g., as described above, so that the blocking moieties are released from the primers to produce activated primers and an activated primer reaction mixture. Where the blocked primers are blocked with enzymatically-labile blocking moieties, unblocking may include introducing an enzyme into the blocked primer reaction mixture, where the enzyme cleaves the enzymatically label blocking moieties from the primers, e.g., as described above, so that the blocking moieties are released from the primers to produce activated primers and an activated primer reaction mixture. Where the blocked primers are blocked with light-labile blocking moieties, unblocking may include exposing the blocked primer reaction mixture to light of wavelength sufficient to cleave the light labile blocking moieties from the primers, e.g., as described above, so that the blocking moieties are released from the primers to produce activated primers and an activated primer reaction mixture.

Following production of the activated primer reaction mixture, e.g., as described above, the resultant activated primer reaction mixture is subjected to template mediated primer extension reaction conditions, such as nucleic acid amplification conditions. Such conditions may vary, where embodiments of such conditions are described in greater detail below.

In some instances, the blocked primers are employed in workflows that include production of a first strand nucleic acid from a template nucleic acid, followed by amplification of the first strand nucleic acid. For example, the above methods may be employed in a workflow that includes producing first strand cDNA (e.g., via a reverse transcriptase) or RNA (e.g., via T7 or SP6 RNA polymerase) from a template nucleic acid, followed by a subsequent amplification step.

1. Template Switch Embodiments

In some embodiments, the above methods are employed in a workflow that includes producing first strand cDNA (or RNA, e.g., via T7 or SP6 RNA polymerase) from a template nucleic acid component via a template switch oligonucleotide protocol, followed by amplification of the resultant cDNA to produce an amplified nucleic acid production composition, which product composition may optionally be further amplified as desired, e.g., to introduce one or more functionalities into the final product composition, such as described in greater detail below.

In such instances, a first strand nucleic acid primer, i.e., a first strand cDNA synthesis primer, hybridizes to a template nucleic acid through complementary sequence shared by the first strand nucleic acid primer and the template nucleic acid. The first strand nucleic acid primer may, but need not necessarily, include a region of additional sequence that is not complementary to the template (e.g., non-templated). In addition, the first strand primer may include one or more ribonucleotides, such as one or more 3' ribonucleotides, e.g., as described in greater detail below.

Following annealing of the first strand nucleic acid primer to the template, reverse transcription proceeds, e.g., through the use of a reverse transcriptase, to generate a single product nucleic acid strand that is complementary to the template, e.g., a first strand cDNA product nucleic acid. The reverse transcriptase, having terminal transferase activity, transfers non-templated nucleotides to the generated single product nucleic acid and a template switching oligonucleotide hybridizes to the non-templated nucleotides of the single product nucleic acid by a sequence of complementary nucleotides present on the template switch oligonucleotide. The template switch oligonucleotide includes additional sequence that does not hybridize to the non-templated nucleotides. Template switching occurs, wherein the reverse transcriptase switches from the template to utilize the template switching oligonucleotide as a second template, transcribing additional sequence to generate its complement. The now fully generated single product nucleic acid strand includes the complete sequence of the first strand nucleic acid primer, including any additional sequence, if present, that did not hybridize to the template, the complementary sequence of the template and the complementary sequence of the template switch oligonucleotide. Methods and reagents related to template switching are also described in U.S. Pat. No. 9,410,173; the disclosure of which is incorporated herein by reference in its entirety.

a. Template Switch Oligonucleotide

A template-switching reverse transcription reaction may make use of a template switch oligonucleotide. By "template switch oligonucleotide" is meant an oligonucleotide template to which a polymerase switches from an initial template (e.g., template nucleic acid (e.g., a RNA template)) during a nucleic acid polymerization reaction. In this regard, the template may be referred to as a "donor template" and the template switch oligonucleotide may be referred to as an "acceptor template." As used herein, an "oligonucleotide" is a single-stranded multimer of nucleotides from 2 to 500 nucleotides, e.g., 2 to 200 nucleotides. Oligonucleotides may be synthetic or may be made enzymatically, and, in some embodiments, are 10 to 50 nucleotides in length. Oligonucleotides may contain ribonucleotide monomers (i.e., may be oligoribonucleotides or "RNA oligonucleotides") or deoxyribonucleotide monomers (i.e., may be oligodeoxyribonucleotides or "DNA oligonucleotides"). Oligonucleotides may be 10 to 20, 21 to 30, 31 to 40, 41 to 50, 51-60, 61 to 70, 71 to 80, 80 to 100, 100 to 150 or 150 to 200, up to 500 or more nucleotides in length, for example.

A template-switching reverse transcription reaction may make use of a suitable reaction mixture. Suitable reaction mixtures for a template-switching reverse transcription reaction may include the template switch oligonucleotide at a concentration sufficient to readily permit template switching of the polymerase from the template to the template switch oligonucleotide and further elongation by a polymerase as templated by any additional sequence, if present, of the template switch oligonucleotide. For example, the template switch oligonucleotide may be added to the reaction mixture at a final concentration of from 0.01 to 100 µM, such as from 0.1 to 10 µM, such as from 0.5 to 5 µM, including 1 to 2 µM (e.g., 1.2 µM).

In a template-switching reverse transcription reaction, a template switch oligonucleotide may or may not include one or more nucleotides (or analogs thereof) that are modified or otherwise non-naturally occurring. For example, the template switch oligonucleotide may include one or more nucleotide analogs (e.g., LNA, FANA, 2'-O-Me RNA, 2'-fluoro RNA, or the like), linkage modifications (e.g., phosphorothioates, 3'-3' and 5'-5' reversed linkages), 5' and/or 3' end modifications (e.g., 5' and/or 3' amino, biotin, DIG, phosphate, thiol, dyes, quenchers, etc.), one or more fluorescently labeled nucleotides, or any other feature that provides a desired functionality to the template switch oligonucleotide.

In certain aspects, the template switch oligonucleotide includes a 3' hybridization domain. The 3' hybridization domain may vary in length, and in some instances ranges from 2 to 10 nts in length, such as 3 to 7 nts in length. The 3' hybridization domain of a template switch oligonucleotide may include a sequence complementary to a non-templated sequence added to a single product nucleic acid of the template-switching reaction (e.g., a cDNA). Non-templated sequences, described in more detail below, generally refer to those sequences that do not correspond to and are not templated by a template, e.g., a RNA template or a DNA template. Where present in the 3' hybridization domain of a template switch oligonucleotide, non-templated sequences may encompass the entire 3' hybridization domain or a portion thereof. In some instances, a non-templated sequence may include or consist of a hetero-polynucleotide, where such a hetero-polynucleotide may vary in length from 2 to 10 nts in length, such as 3 to 7 nts in length, including 3 nts. In some instances, a non-templated sequence may include or consist of a homo-polynucleotide, where such a homo-polynucleotide may vary in length from 2 to 10 nts in length, such as 3 to 7 nts in length, including 3 nts.

b. Tail Sequences and Tailing

In some instances, the present methods may include generating a double stranded product cDNA and/or amplifying a template nucleic acid having a tail sequence using a primer having a sequence that is complementary to the tail sequence. The term "tail sequence", as used herein, generally refers to a polynucleotide stretch present on the 3' end of the template nucleic acid made up of a single nucleotide species (e.g., A, C, G, T, etc.). In some instances, a first strand complementary deoxyribonucleic acid (cDNA) primer may be, in whole or in part, complementary to a tail sequence. For example, a poly(A) tail of a mRNA template is one non-limiting example of a tail sequence. Accordingly, a first strand cDNA primer may, in some instances, include or consist of a poly(T) sequence that is complementary to the poly(A) tail of a mRNA template.

Tail sequences may be naturally present on a subject template nucleic acid or may be synthetically added. Accordingly, examples of tail sequences that may be present on a subject template nucleic acid include but are not limited to e.g., a poly(A) tail, a poly(C) tail, a poly(G) tail, a poly(T) tail, and the like. Tail sequences may range in size from less than 10 nt to 300 nt or more, including but not limited to e.g., 10 to 300 nt, 10 to 200 nt, 10 to 150 nt, 10 to 100 nt, 10 to 90 nt, 10 to 80 nt, 10 to 70 nt, 10 to 60 nt, 10 to 50 nt, 10 to 40 nt, 10 to 30 nt, 10 to 20 nt, 20 to 300 nt, 20 to 200 nt, 20 to 150 nt, 20 to 100 nt, 20 to 90 nt, 20 to 80 nt, 20 to 70 nt, 20 to 60 nt, 20 to 50 nt, 20 to 40 nt, 20 to 30 nt, 15 nt, 16 nt, 18 nt, 20 nt, etc. Where a template nucleic acid contains a tail sequence, a primer utilized in generating a double stranded product cDNA, e.g., a first strand cDNA primer, may contain a sequence complementary to the tail sequence to which the primer hybridizes and primes elongation of the first strand cDNA. Useful sequences complementary to the tail sequence will vary and may include but are not limited to e.g., a poly(dA) sequence, a poly(dC) sequence, a poly(dG) sequence, a poly(dT) sequence, and the like.

As noted above, tail sequences present on template nucleic acids may be naturally occurring (e.g., in the case of the poly(A) tail of an mRNA template) or may be artificially or synthetically produced. For example, in some instances, a tail sequence may be added to a nucleic acid template, in a tailing reaction. Tailing reactions will vary and may include, e.g., where the tail sequence is added to the template through an enzymatic process. Useful enzymes for tailing a subject nucleic acid template include but are not limited to e.g., terminal transferase (e.g., Terminal Deoxynucleotidyl Transferase, RNA-specific nucleotidyl transferases, and the like). The nucleotide specie of the tailing sequence may be controlled as desired, e.g., by making available in a tailing reaction utilizing a terminal transferase only the desired species of dNTP (e.g., only dATP, only dCTP, only dGTP or only dTTP). In some instances, a "dNTP tailing mix" is used in a tailing reaction where such a mix contains only one species of dNTP (e.g., ATP). In some instances, a nucleic acid template may be prepared for a tailing reaction e.g., by removal of a 3' phosphate (dephosphorylation) present on the nucleic acid template. Any convenient and appropriate phosphatase may be employed for such purposes including but not limited to e.g., Alkaline Phosphatase (e.g., Shrimp Alkaline Phosphatase and derivative thereof), and the like.

In some instances, the subject methods may include performing a tailing reaction to add a tailing sequence to a template nucleic acid, e.g., by contacting a template nucleic acid with a terminal transferase in the presence of a species of dNTP under conditions sufficient to produce the template having the tail sequence (i.e., a tailed template). The rate of addition of dNTPs—and thus the length of tail sequence—is a function of the ratio of 3' ends to the dNTP concentration, and also which dNTP is used. The terminal transferase reaction is carried out at a temperature at which the terminal transferase is active, such as between 30° C. and 50° C., including 37° C. The dNTPs in the terminal transferase reaction may be present at a final concentration of from 0.01 mM to 1 mM, such as from 0.05 mM to 0.5 mm, including 0.1 mM. The template nucleic acid may be present in the terminal transferase reaction at a concentration of from 0.05 to 500 pmol, such as from 0.5 to 50 pmol, including 1 to 25 pmol, e.g., 5 pmol. A terminal transferase buffer solution and any other useful components (e.g., a metal cofactor such as Co, or the like) may also be included in the terminal transferase reaction, e.g., as a separate solution (e.g., buffer) or as part of a "dNTP tailing mix". The terminal transferase reaction results in the addition of nucleotides at the 3' end of the nucleic acid template and the resulting tailed-template nucleic acid may then be utilized in further steps of the reaction according to the subject methods.

In some instances, a template switch oligonucleotide includes a modification that prevents the polymerase from switching from the template switch oligonucleotide to a different template nucleic acid after synthesizing the compliment of the 5' end of the template switch oligonucleotide (e.g., a 5' adapter sequence of the template switch oligonucleotide). Useful modifications include, but are not limited to, an abasic lesion (e.g., a tetrahydrofuran derivative), a nucleotide adduct, an iso-nucleotide base (e.g., isocytosine, isoguanine, and/or the like), and any combination thereof.

In some instances, a template switch oligonucleotide may include a 5' adapter sequence (e.g., a defined nucleotide sequence 5' of the 3' hybridization domain of the template switch oligonucleotide), the 5' adapter sequence may serve various purposes in downstream applications. In some instances, the 5' adapter sequence may serve as a primer binding site for further amplification or, e.g., nested amplification or suppression amplification, of the amplified dsDNA.

c. Primers

As summarized above, a single product nucleic acid primer, also referred to as a single product nucleic acid synthesis primer (e.g., a first strand cDNA primer) or a first strand primer, includes a template binding domain. For example, the nucleic acid may include a first (e.g., 3') domain that is configured to hybridize to a template nucleic acid, e.g., mRNA, etc., and may or may not include one or more additional domains which may be viewed as a second (e.g., 5') domain that does not hybridize to the template nucleic acid, e.g., a non-template sequence domain as described in more detail below. In addition, the first strand primer may include one or more ribonucleotides, such as one or more 3' ribonucleotides, e.g., as described in greater detail below. The sequence of the template binding domain may be independently defined or arbitrary. In certain aspects, the template binding domain has a defined sequence, e.g., poly dT or gene specific sequence. In other aspects, the template binding domain has an arbitrary sequence (e.g., a random sequence, such as a random hexamer sequence). While the length of the template binding domain may vary, in some instances the length of this domain ranges from 5 to 50 nts, such as 6 to 25 nts, e.g., 6 to 20 nts.

The single product nucleic acid primer may or may not include one or more nucleotides (or analogs thereof) that are modified or otherwise non-naturally occurring. For example, the single product nucleic acid primer may include one or more nucleotide analogs (e.g., LNA, FANA, 2'-O-Me RNA, 2'-fluoro RNA, or the like), linkage modifications (e.g., phosphorothioates, 3'-3' and 5'-5' reversed linkages), 5' and/or 3' end modifications (e.g., 5' and/or 3' amino, biotin, DIG, phosphate, thiol, dyes, quenchers, etc.), one or more fluorescently labeled nucleotides, or any other feature that provides a desired functionality to the single product nucleic acid primer.

In some instances, a single product nucleic acid primer may include a 5' adapter sequence (e.g., a defined nucleotide sequence 5' of the 3' hybridization domain of the single product nucleic acid primer), the 5' adapter sequence may serve various purposes in downstream applications. In some instances, the 5' adapter sequence may serve as a primer binding site for further amplification or, e.g., nested amplification or suppression amplification.

In some instances, one or more of the primers or oligonucleotides employed (including e.g., single product nucleic acid primers, template switch oligonucleotides, etc.) may include two or more domains. For example, the primer or oligonucleotide may include a first (e.g., 3') domain that hybridizes to a template and a second (e.g., 5') domain that does not hybridize to a template. The sequence of the first and second domains may be independently defined or arbitrary. In certain aspects, the first domain has a defined sequence and the sequence of the second domain is defined or arbitrary. In other aspects, the first domain has an arbitrary sequence (e.g., a random sequence, such as a random hexamer sequence) and the sequence of the second domain is defined or arbitrary. In some instances, the sequences of both domains are defined. Where a primer (including e.g., single product nucleic acid primers, template switch oligonucleotides, etc.) utilized in the subject methods includes two or more domains, one or more of the domains may include a non-templated sequence as described below.

Where desired, one or more of the above primers may be blocked, e.g., as described above.

d. Polymerases

In some instances, a polymerase combined into a template-switching reverse transcription reaction mixture is capable of template switching, where the polymerase uses a first nucleic acid strand as a template for polymerization, and then switches to the 3' end of a second template nucleic acid strand to continue the same polymerization reaction. In some instances, the polymerase capable of template switching is a reverse transcriptase. Reverse transcriptases capable of template-switching that find use in practicing the subject methods include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants derivatives, or functional fragments thereof, e.g., RNase H minus or RNase H reduced enzymes. For example, the reverse transcriptase may be a Moloney Murine Leukemia Virus reverse transcriptase (MMLV RT) or a Bombyx mori reverse transcriptase (e.g., Bombyx mori R2 non-LTR element reverse transcriptase). Polymerases capable of template switching that find use in practicing the subject methods are commercially available and include SMARTScribe™ reverse transcriptase and PrimeScript™ reverse transcriptase available from Takara Bio USA, Inc. (Mountain View, Calif.).

A template-switching reverse transcription reaction of the present methods may include the use of a polymerase having terminal transferase activity. For example, the polymerase (e.g., a reverse transcriptase such as MMLV RT) combined into the reaction mixture has terminal transferase activity such that a nucleotide stretch, such as a homonucleotide stretch or heteronucleotide stretch (e.g., made up of Gs and/or Cs) may be added to the 3' end of a nascent strand, and the 3' hybridization domain of the template switch oligonucleotide includes a complementary stretch that is complementary to that of the 3' end of the nascent strand. In other aspects, when the polymerase having terminal transferase activity adds a nucleotide stretch to the 3' end of the nascent strand (e.g., a trinucleotide stretch), the 3' hybridization domain of the template switch oligonucleotide includes a hetero-trinucleotide comprises a nucleotide comprising cytosine and a nucleotide comprising guanine (e.g., an $r(C/G)_3$ oligonucleotide), which hetero-trinucleotide stretch of the template switch oligonucleotide is complementary to the 3' end of the nascent strand. Examples of 3' hybridization domains and template switch oligonucleotides are further described in U.S. Pat. No. 5,962,272, the disclosure of which is herein incorporated by reference.

A polymerase with terminal transferase activity is capable of catalyzing the addition of deoxyribonucleotides to the 3' hydroxyl terminus of a RNA or DNA molecule. In certain aspects, when the polymerase reaches the 5' end of the template, the polymerase is capable of incorporating one or more additional nucleotides at the 3' end of the nascent strand not encoded by the template. For example, when the polymerase has terminal transferase activity, the polymerase may be capable of incorporating 1, 2, 3, 4, 5, 6, 7, 8, 9, 10 or more additional nucleotides at the 3' end of the nascent strand. All of the nucleotides may be the same (e.g., creating a homonucleotide stretch at the 3' end of the nascent strand) or one or more of the nucleotides may be different from the other(s) (e.g., creating a heteronucleotide stretch at the 3' end of the nascent strand). In certain aspects, the terminal transferase activity of the polymerase results in the addition of a homonucleotide stretch of 2, 3, 4, 5, 6, 7, 8, 9, 10 or more of the same nucleotides (e.g., all dCTP, all dGTP, all dATP, or all dTTP). For example, according to one embodiment, the polymerase is an MMLV reverse transcriptase (MMLV RT). MMLV RT incorporates additional nucleotides (predominantly dCTP, e.g., three dCTPs) at the 3' end of the nascent strand. As described in greater detail elsewhere herein, these additional nucleotides may be useful for enabling hybridization between a 3' hybridization domain of a template switch oligonucleotide and the 3' end of the nascent strand, e.g., to facilitate template switching by the polymerase from the template to the template switch oligonucleotide.

Reverse transcriptase utilized in the subject methods may, in some instances, be a thermo-sensitive polymerase, i.e., a polymerase that is not thermostable. Such thermo-sensitive polymerases may become inactive at a temperature above their active temperature range. For example, in some instances, a thermos-sensitive polymerase may become inactive or demonstrate significantly reduced activity after being exposed to temperatures of 75° or higher, 80° or higher, 85° or higher, 90° or higher or 95° or higher.

Where a reverse transcriptase is employed, it may be combined into the reaction mixture such that the final concentration of the reverse transcriptase is sufficient to produce a desired amount of the RT reaction product, e.g., a desired amount of a single product nucleic acid. In certain aspects, the reverse transcriptase (e.g., an MMLV RT, a Bombyx mori RT, etc.) is present in the reaction mixture at a final concentration of from 0.1 to 200 units/μL (U/μL), such as from 0.5 to 100 U/μL, such as from 1 to 50 U/μL, including from 5 to 25 U/μL, e.g., 20 U/μL.

e. Non-Templated Sequences and Non-Template Sequences

Aspects of the described methods may, in some instances, include the use of non-templated sequences. The terms "non-templated sequence" and "non-template sequence" generally refer to those sequences involved in the subject method that do not correspond to the template (e.g., are not present in the templates, do not have a complementary sequence in the template or are unlikely to be present in or have a complementary sequence in the template). Non-templated sequences are those that are not templated by a template, e.g., a RNA or DNA template, thus they may be, e.g., added during an elongation reaction in the absence of corresponding template, e.g., nucleotides added by a polymerase having non-template directed terminal transferase activity. The addition of non-templated sequence to a nucleic acid need not be necessarily limited to elongation reaction. For example, in some instances, a non-templated sequence may be added through ligation of the non-templated sequence to the nucleic acid. Accordingly, non-templated sequences may vary and may be added to templated sequence through a variety of means.

Non-template and non-templated sequence may, but not exclusively, refer to those sequences present on a primer or template switch oligonucleotide that do not hybridize to the nucleic acid template (such sequences may, in some instances, be referred to as non-hybridizing sequence). Non-templated sequence will vary, in both size and composition. In some instances, non-templated sequence, e.g., non-templated sequence present on a template switch oligonucleotide or a primer, may range from 10 nt to 1000 nt or more including but not limited to e.g., 10 nt to 900 nt, 10 nt to 800 nt, 10 nt to 700 nt, 10 nt to 600 nt, 10 nt to 500 nt, 10 nt to 400 nt, 10 nt to 300 nt, 10 nt to 200 nt, 10 nt to 100 nt, 10 nt to 90 nt, 10 nt to 80 nt, 10 nt to 70 nt, 10 nt to 60 nt, 10 nt to 50 nt, 10 nt to 40 nt, 10 nt to 30 nt, 10 nt to 20 nt, etc.

In some instances, a non-templated sequence, as noted above, may be included in the 3' hybridization domain of a template switch oligonucleotide. When present in the 3' hybridization domain of a template switch oligonucleotide, a non-templated sequence may include or consist of a hetero-polynucleotide, where such a hetero-polynucleotide may vary in length from 2 to 10 nts in length, such as 3 to 7 nts in length, including 3 nts. In some instances, a non-templated sequence present in the 3' hybridization domain of a template switch oligonucleotide may include or consist of a homo-polynucleotide, where such a homo-polynucleotide may vary in length from 2 to 10 nts in length, such as 3 to 7 nts in length, including 3 nts.

Non-templated sequences present on an oligonucleotide or a primer may be present at the 5' end of the oligonucleotide or primer and may, in such instances, be referred to as a 5' non-templated sequence. In some instances, only one oligonucleotide or primer may include a non-templated sequence (e.g., a 5' non-templated sequence) in a subject reaction. In some instances, two or more oligonucleotides and/or primers utilized in a subject reaction may include a non-templated sequence (e.g., a 5' non-templated sequence). Where two or more oligonucleotides and/or primers include a non-templated sequence, different non-templated sequences may be employed. In some instances, where two or more oligonucleotides and/or primers have a 5' non-templated sequence, such sequences may have the same 5' non-templated sequence.

In some instances, non-templated sequence, including e.g., 5' non-templated sequence, may include one or more primer binding sites. In some instances, one or more primer binding sites may be incorporated into a subject nucleic acid allowing further amplification of the produced nucleic acid, including e.g., amplifying all or a portion of the nucleic acid using one or more of the primer binding sites.

Useful primer binding sites will vary widely depending on the desired complexity of the primer binding site and the corresponding primer. In some instances, useful primer binding sites include those having complementarity to a II A primer (e.g., as available from Takara Bio USA, Inc., Mountain View, Calif.). According to one embodiment, an oligonucleotide or a primer utilized in generating a product double stranded cDNA includes a non-template sequence that includes a II A primer binding site. According to one embodiment, a nucleic acid utilized in an end capturing reaction includes a non-template sequence that includes a II A primer binding site.

In some instances, non-templated sequence, including e.g., 5' non-templated sequence, may include one or more barcode sequences. In some instances, such barcode sequences may be or may include a unique molecular identifier (UMI) domain and/or a barcoded unique molecular identifier (BUMI) domain. UMI and BUMI nucleic acids, and their use in various applications, are further described in U.S. Provisional Patent Application No. 62/401,676, filed Sep. 29, 2016; the disclosure of which is incorporated herein by reference in their entirety.

In some instances, one or more barcode sequences of a non-templated sequence may provide for retrospective identification of the source of a generated nucleic acid, e.g., following a sequencing reaction where the barcode is sequenced. For example, in some instances, a non-templated sequence that includes a barcode specific for the source (e.g., sample, well, cell, etc.) of the template is incorporated during a reaction. Such source identifying barcodes may be referred to herein as a "source barcode sequence" and such sequences may vary and may be assigned a term based on the source that is identified by the barcode. Source barcodes may include e.g., a sample barcode sequence that retrospectively identifies the sample from which the sequenced nucleic acid was generated, a well barcode sequence that retrospectively identifies the well (e.g., of a multi-well plate) from which the sequenced nucleic acid was generated, a droplet barcode sequence that retrospectively identifies the droplet from which the sequenced nucleic acid was generated, a cell barcode sequence that retrospectively identifies the cell (e.g., of a multi-cellular sample) from which the sequenced nucleic acid was generated, etc. Barcodes may find use in various procedures including e.g., where nucleic acids are pooled following barcoding, e.g., prior to sequencing.

In some instances, a non-templated sequence, e.g., present on an oligonucleotide and/or a nucleic acid primer, includes a sequencing platform adapter construct. By "sequencing platform adapter construct" is meant a nucleic acid construct that includes at least a portion of a nucleic acid domain (e.g., a sequencing platform adapter nucleic acid sequence) or complement thereof utilized by a sequencing platform of interest, such as a sequencing platform provided by Illumina® (e.g., the HiSeq™, MiSeq™ and/or Genome Analyzer™ sequencing systems); Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems); or any other sequencing platform of interest.

In certain aspects, a non-templated sequence includes a sequencing platform adapter construct that includes a nucleic acid domain that is a domain (e.g., a "capture site" or "capture sequence") that specifically binds to a surface-attached sequencing platform oligonucleotide (e.g., the P5 or P7 oligonucleotides attached to the surface of a flow cell in an Illumina® sequencing system); a sequencing primer binding domain (e.g., a domain to which the Read 1 or Read 2 primers of the Illumina® platform may bind). The sequencing platform adapter constructs may include nucleic acid domains (e.g., "sequencing adapters") of any length and sequence suitable for the sequencing platform of interest. In certain aspects, the nucleic acid domains are from 4 to 200 nts in length. For example, the nucleic acid domains may be from 4 to 100 nts in length, such as from 6 to 75, from 8 to 50, or from 10 to 40 nts in length. According to certain embodiments, the sequencing platform adapter construct includes a nucleic acid domain that is from 2 to 8 nts in length, such as from 9 to 15, from 16-22, from 23-29, or from 30-36 nts in length.

The nucleic acid domains may have a length and sequence that enables a polynucleotide (e.g., an oligonucleotide) employed by the sequencing platform of interest to specifically bind to the nucleic acid domain, e.g., for solid phase amplification and/or sequencing by synthesis of the cDNA insert flanked by the nucleic acid domains. Example nucleic acid domains include the P5 (5'-AATGATACGGCGAC-CACCGA-3') (SEQ ID NO:01), P7 (5'-CAAGCAGAA-GACGGCATACGAGAT-3') (SEQ ID NO:02), Read 1 primer (5'-ACACTCTTTCCCTACACGACGCTCTTCC-GATCT-3') (SEQ ID NO:03) and Read 2 primer (5'-GTGACTGGAGTTCAGACGTGTGCTCTTCCGATCT-3') (SEQ ID NO:03) domains employed on the Illumina®-based sequencing platforms. Other example nucleic acid domains include the A adapter (5'-CCATCT-CATCCCTGCGTGTCTCCGACTCAG-3') (SEQ ID NO:05) and P1 adapter (5'-CCTCTC-TATGGGCAGTCGGTGAT-3') (SEQ ID NO:06) domains employed on the Ion Torrent™-based sequencing platforms.

The nucleotide sequences of non-templated sequence domains useful for sequencing on a sequencing platform of interest may vary and/or change over time. Adapter sequences are typically provided by the manufacturer of the sequencing platform (e.g., in technical documents provided with the sequencing system and/or available on the manufacturer's website). Based on such information, the sequence of the sequencing platform adapter construct of the non-templated sequence (e.g., a template switch oligonucleotide and/or a single product nucleic acid primer, and/or the like) may be designed to include all or a portion of one or more nucleic acid domains in a configuration that enables sequencing the nucleic acid insert (corresponding to the template nucleic acid) on the platform of interest. Sequencing platform adaptor constructs that may be included in a non-templated sequence as well as other nucleic acid reagents described herein, are further described in U.S. patent application Ser. No. 14/478,978 published as US 2015-0111789 A1, the disclosure of which is herein incorporated by reference.

Non-templated sequence may be added to a nucleic acid of interest, e.g., to an oligonucleotide, a nucleic acid primer, a generated dsDNA, etc., by a variety of means. For example, as noted above, non-templated sequence may be added through the action of a polymerase with terminal transferase activity. Non-templated sequence, e.g., present on a primer or oligonucleotide, may be incorporated into a product nucleic acid during an amplification reaction. In some instances, non-templated nucleic acid sequence may be directly attached to a nucleic acid, e.g., to a primer or oligonucleotide prior to amplification, to a product of nucleic acid amplification, etc. Methods of directly attaching a non-templated sequence to a nucleic acid will vary and may include but are not limited to e.g., ligation, chemical synthesis/linking, enzymatic nucleotide addition (e.g., by a polymerase with terminal transferase activity), and the like.

In some instances, the methods may include attaching sequencing platform adapter constructs to ends of a nucleic acid. For example, in some instances, oligonucleotides and/or primers utilized in the subject methods may not include sequencing platform adapter constructs and thus desired sequencing platform adapter constructs may be attached following the production of a nucleic acid of interest.

Adapter constructs attached to the ends of a nucleic acid of interest or a derivative thereof may include any sequence elements useful in a downstream sequencing application, including any of the elements described above with respect to the optional sequencing platform adapter constructs of the oligonucleotides and/or primers of the herein described methods. For example, the adapter constructs attached to the ends of nucleic acid of interest or a derivative thereof may include a nucleic acid domain or complement thereof selected from the group consisting of: a domain that specifically binds to a surface-attached sequencing platform oligonucleotide, a sequencing primer binding domain, a barcode domain, a barcode sequencing primer binding domain, a molecular identification domain, and combinations thereof.

Attachment of the sequencing platform adapter constructs may be achieved using any suitable approach. In certain aspects the adapter constructs are attached to the ends of the product nucleic acid or a derivative thereof using an approach that is the same or similar to "seamless" cloning strategies. Seamless strategies eliminate one or more rounds of restriction enzyme analysis and digestion, DNA end-repair, de-phosphorylation, ligation, enzyme inactivation and clean-up, and the corresponding loss of nucleic acid material. Seamless attachment strategies of interest include: the In-Fusion® cloning systems available from Takara Bio USA, Inc. (Mountain View, Calif.), SLIC (sequence and ligase independent cloning) as described in Li & Elledge (2007) *Nature Methods* 4:251-256; Gibson assembly as described in Gibson et al. (2009) *Nature Methods* 6:343-345; CPEC (circular polymerase extension cloning) as described in Quan & Tian (2009) *PLoS ONE* 4(7): e6441; SLiCE (seamless ligation cloning extract) as described in Zhang et al. (2012) *Nucleic Acids Research* 40(8): e55, and the GeneArt® seamless cloning technology by Life Technologies (Carlsbad, Calif.).

Any suitable approach may be employed for providing additional nucleic acid sequencing domains to a nucleic acid of interest or derivative thereof having less than all of the useful or necessary sequencing domains for a sequencing platform of interest. For example, a nucleic acid of interest or derivative thereof could be amplified using PCR primers having adapter sequences at their 5' ends (e.g., 5' of the region of the primers complementary to the nucleic acid of interest or derivative thereof), such that the amplicons include the adapter sequences in the original nucleic acid as well as the adapter sequences in the primers, in any desired configuration. Other approaches, including those based on seamless cloning strategies, restriction digestion/ligation, or the like may be employed.

2. Additional Method Parameters

As summarized above, the herein described method may include certain nucleic acid reactions, including e.g., template-switching reverse transcription reactions, nucleic acid amplification reactions, and the like. The reaction mixture components in such reactions are combined under conditions sufficient to produce the product of the reaction. For example, in some instances, the reaction components of a template-switching reverse transcription reaction are combined under conditions sufficient to produce a product double stranded cDNA. In some instances, the reaction components of a nucleic acid amplification reaction are combined under conditions sufficient to produce an amplified product nucleic acid.

By "conditions sufficient to produce" the subject nucleic acid is meant reaction conditions that permit the relevant nucleic acids and/or other reaction components in the reaction to interact with one another in the desired manner. For example, in some instances, the conditions may be sufficient for nucleic acids of the reaction mixture to hybridize. In some instances, the conditions may be sufficient for an enzyme of the reaction mixture to catalyze a chemical process such as e.g., polymerization, hydrolysis, etc. Achieving suitable reaction conditions may include selecting reaction mixture components, concentrations thereof, and a reaction temperature to create an environment in which the relevant processes proceed, including e.g., the relevant nucleic acids hybridize with one another in a sequence specific manner, the relevant polymerase polymerizes resulting in elongation of a nucleic acid, etc. In addition to specific nucleic acids (e.g., template nucleic acids, oligonucleotides, primers, etc.) of a reaction the reaction mixture may include buffer components that establish an appropriate pH, salt concentration (e.g., KCl concentration), etc. Conditions sufficient to produce a double stranded nucleic acid complex may include those conditions appropriate for hybridization, also referred to as "hybridization conditions".

Achieving suitable reaction conditions may include selecting reaction mixture components, concentrations thereof, and a reaction temperature to create an environment in which one or more polymerases are active and/or the relevant nucleic acids in the reaction interact (e.g., hybridize) with one another in the desired manner. In suitable reaction conditions, in addition to reaction components, the reaction mixture may include buffer components that establish an appropriate pH, salt concentration (e.g., KCl concentration), metal cofactor concentration (e.g., $Mg^{2+}$ or $Mn^{2+}$ concentration), and the like, for the extension reaction(s) and/or template switching to occur. Other components may be included, such as one or more nuclease inhibitors (e.g., an RNase inhibitor and/or a DNase inhibitor), one or more additives for facilitating amplification/replication of GC rich sequences (e.g., GC-Melt™ reagent (Takara Bio USA, Inc. (Mountain View, Calif.)), betaine, DMSO, ethylene glycol, 1,2-propanediol, or combinations thereof), one or more molecular crowding agents (e.g., polyethylene glycol, or the like), one or more enzyme-stabilizing components (e.g., DTT present at a final concentration ranging from 1 to 10 mM (e.g., 5 mM)), and/or any other reaction mixture components useful for facilitating polymerase-mediated extension reactions and/or template-switching.

One or more reaction mixtures may have a pH suitable for a primer extension reaction and/or template-switching. In certain embodiments, the pH of the reaction mixture ranges from 5 to 9, such as from 7 to 9, including from 8 to 9, e.g., 8 to 8.5. In some instances, the reaction mixture includes a pH adjusting agent. pH adjusting agents of interest include, but are not limited to, sodium hydroxide, hydrochloric acid, phosphoric acid buffer solution, citric acid buffer solution, and the like. For example, the pH of the reaction mixture can be adjusted to the desired range by adding an appropriate amount of the pH adjusting agent.

The temperature range suitable for primer extension reactions may vary according to factors such as the particular polymerase employed, the melting temperatures of any primers employed, etc. In some instances, a reverse transcriptase (e.g., an MMLV reverse transcriptase) may be employed and the reaction mixture conditions sufficient for reverse transcriptase-mediated extension of a hybridized primer include bringing the reaction mixture to a temperature ranging from 4° C. to 72° C., such as from 16° C. to 70° C., e.g., 37° C. to 50° C., such as 40° C. to 45° C., including 42° C.

In some instances, the methods described herein may include denaturing the template, e.g., by subjecting a reaction mixture containing the template to a temperature sufficient to denature secondary structure of the template. Depending on the context, denaturing may take place before or after one or more reaction components have been added to the reaction mixture and, in some instances, is performed prior to the start of transcription, e.g., reverse transcription to generate the single product nucleic acid. Useful denaturing temperatures will vary and may range from less than 50° C. to more than 100° C., including but not limited to e.g., 50° C. or more, 55° C. or more, 65° C. or more, 70° C. or more, 72° C. or more, 75° C. or more, 80° C. or more, 85° C. or more, 90° C. or more, 95° C. or more, etc.

In some instances, methods provided may include isolating and/or purifying a final nucleic acid product (e.g., a nucleic acid library) and/or an intermediate nucleic acid product (e.g., a double stranded product cDNA). Any convenient method of purification may be employed including but not limited to e.g., nucleic acid precipitation (i.e., alcohol precipitation), gel purification, etc.

In some instances, methods provided may include the use of an amplification polymerase, e.g., for use in amplifying a produced double stranded cDNA, a produced nucleic acid library, etc. Any convenient amplification polymerase may be employed including but not limited to DNA polymerases including thermostable polymerases. Useful amplification polymerases include e.g., Taq DNA polymerases, Pfu DNA polymerases, derivatives thereof and the like. In some instances, the amplification polymerase may be a hot start polymerase including but not limited to e.g., a hot start Taq DNA polymerase, a hot start Pfu DNA polymerase, and the like.

An amplification polymerase may be combined into a reaction mixture such that the final concentration of the amplification polymerase is sufficient to produce a desired amount of the product nucleic acid, e.g., a desired amount of amplified product double stranded cDNA, a desired amount of library nucleic acid, etc. In certain aspects, the amplification polymerase (e.g., a thermostable DNA polymerase, a hot start DNA polymerase, etc.) is present in the reaction mixture at a final concentration of from 0.1 to 200 units/μL (U/μL), such as from 0.5 to 100 U/μL, such as from 1 to 50 U/μL, including from 5 to 25 U/μL, e.g., 20 U/μL.

Nucleic acid reactions, e.g., amplification reactions, of the subject methods may include combining dNTPs into a reaction mixture. In certain aspects, each of the four naturally-occurring dNTPs (dATP, dGTP, dCTP and dTTP) are added to the reaction mixture. For example, dATP, dGTP, dCTP and dTTP may be added to the reaction mixture such that the final concentration of each dNTP is from 0.01 to 100 mM, such as from 0.1 to 10 mM, including 0.5 to 5 mM (e.g., 1 mM). In some instances, one or more types of nucleotide added to the reaction mixture may be a non-naturally occurring nucleotide, e.g., a modified nucleotide having a binding or other moiety (e.g., a fluorescent moiety) attached thereto, a nucleotide analog, or any other type of non-naturally occurring nucleotide that finds use in the subject methods or a downstream application of interest.

In addition to the reagents described above, amplification reaction mixtures may include at least one pair of amplification primers, which pair of amplification primers may be blocked, e.g., as described above. Depending on a given workflow, a give protocol may employ the use of two or more sets of different amplification primers, e.g., where two or more rounds of amplification are performed, such as described in greater detail below. In such instances, only one of the multiple pairs of amplification primers may be blocked, or two or more pairs of the multiple pairs, including all of the pairs of the multiple pairs of amplification primers, may be blocked, e.g., with differential blocking moieties, such as described above.

Reaction mixtures may be subjected to various temperatures to drive various aspects of the reaction including but not limited to e.g., denaturing/melting of nucleic acids, hybridization/annealing of nucleic acids, polymerase-mediated elongation/extension, etc. Temperatures at which the various processes are performed may be referred to according to the process occurring including e.g., melting temperature, annealing temperature, elongation temperature, etc. The optimal temperatures for such processes will vary, e.g., depending on the polymerase used, depending on characteristics of the nucleic acids, etc. Optimal temperatures for particular polymerases, including reverse transcriptases and amplification polymerases, may be readily obtained from reference texts. Optimal temperatures related to nucleic acids, e.g., annealing and melting temperatures may be readily calculated based on known characteristics of the subject nucleic acid including e.g., overall length, hybridization length, percent G/C content, secondary structure prediction, etc.

Where desired, a given embodiment of the invention may include a pooling step. In protocols that include a pooling step, the pooling step can be performed after production of an initial amplified product nucleic acid composition, as desired. Where desired, a given single cell or droplet workflow may include a pooling step where a nucleic acid product composition, e.g., made up of an initial amplified product composition, is combined or pooled with the nucleic acid product compositions obtained from one or more additional cells or droplets. The number of different nucleic acid product compositions produced from different cells or droplets that are combined or pooled in such embodiments may vary, where the number ranges in some instances from 2 to 50, such as 3 to 25, including 4 to 20 or 10,000, or more.

3. Analyzing Nucleic Acids

According to certain embodiments, the subject methods may include isolating, amplifying and/or analyzing (e.g., sequencing) a deoxyribonucleic acid (DNA). Where the subject methods include isolating, amplifying and/or analyzing DNA the DNA employed may be referred to as a DNA template (or sometimes referred to as template DNA). Template DNAs may be any type of DNA (or sub-type thereof) including, but not limited to, genomic DNA (e.g., animal genomic DNA (e.g., mammalian genomic DNA (e.g., human genomic DNA, rodent genomic DNA (e.g., mouse, rat, etc.), etc.), mitochondrial DNA, or any combination of DNA types thereof or subtypes thereof.

In certain embodiment, genomic DNA (gDNA) may be isolated and/or processed for analysis as desired. For example, in some instances, the provided methods may include the preparation of one or more libraries from a sample containing RNA and further include isolating, processing and/or analyzing gDNA from the sample. Accordingly, in some instances, samples may include those that contain both RNA and DNA (e.g., gDNA), including e.g., nucleic acid samples isolated from a plurality of cells and samples isolated from a single cell. For example, in some instances, the subject methods may include isolating, processing and/or analyzing RNA and DNA from a single cell, including where e.g., processing of the RNA includes the preparation of two or more libraries (e.g., an expression library and an immune cell receptor repertoire library) from the RNA sample.

Isolating, processing and/or analyzing of gDNA may be performed for a variety of purposes. For example, in some instances, the gDNA of a sample may be sequenced to obtain genomic sequence information. Such sequencing of gDNA of a subject sample may, in some instances, include sequencing an immune locus or one or more immune loci. By "immune locus" is generally meant a genetic locus of any immune related gene, including those genes associated with immune system process (such as the genes identified by gene ontology (GO) accession number GO:0002376 (available online at geneontology(dot)org) including but not limited to e.g., those genes associated with B cell mediated immunity, B cell selection, T cell mediated immunity, T cell selection, activation of immune response, antigen processing and presentation, antigen sampling in mucosal-associated lymphoid tissue, basophil mediated immunity, eosinophil mediated immunity, hemocyte differentiation, hemocyte proliferation, immune effector process, immune response, immune system development, immunological memory process, leukocyte activation, leukocyte homeostasis, leukocyte mediated immunity, leukocyte migration, lymphocyte costimulation, lymphocyte mediated immunity, mast cell mediated immunity, myeloid cell homeostasis, myeloid leukocyte mediated immunity, natural killer cell mediated immunity, negative regulation of immune system process, neutrophil mediated immunity, positive regulation of immune system process, production of molecular mediator of immune response, regulation of immune system process, somatic diversification of immune receptors, tolerance induction, and the like.

In some instances, an immune locus that may be sequenced and/or otherwise analyzed in the subject methods may be a TCR locus. In some instances, an immune locus that may be sequenced and/or otherwise analyzed in the subject methods may be a BCR locus. In some instances, sequencing the gDNA of an immune locus may allow for coordinated analysis with one or more NGS analyses of a library produced herein, including e.g., an expression library and/or an immune cell receptor repertoire library. In some instances, gDNA analysis performed in the provided methods may include whole genome sequencing.

4. Immune Cell Repertoires

In some embodiments the present methods include preparing an immune cell receptor repertoire library from an RNA sample. Aspects of the subject methods include amplifying an immune cell-specific cDNA from a product double stranded cDNA generated from a RNA sample to produce an immune cell receptor repertoire library. By "immune cell receptor repertoire library" is generally meant a nucleic acid library that includes full length or partial sequences of one or more types of immune receptors of a cell or a population of cells. For example, an immune cell receptor repertoire library may be generated for a single cell or for a population of cells derived from a single cellular sample or a single subject or a population of cellular samples, including e.g., a population of samples from two or more subjects. In some instances, a subject library may be generated from individual single cells which, following the addition of an identifying nucleic acid sequence, may be pooled.

As noted above, the members of an immune cell receptor repertoire library may vary in length and may be full length or less than full length. In some instances, the members of the library will preferentially include the 5' end of an immune cell receptor. Immune cell receptors of interest include but are not limited to e.g., the T-cell receptor (TCR) and the B-cell receptor (BCR).

In some instances, an immune cell receptor repertoire library may include a TCR repertoire library. The TCR complex is a disulfide-linked membrane-anchored heterodimeric protein normally expressed on the surface of T cells and consisting of the highly variable alpha ($\alpha$) and beta ($\beta$) chains expressed as part of a complex with CD3 chain molecules. Many native TCRs exist in heterodimeric $\alpha\beta$ or $\gamma\delta$ forms. The complete endogenous TCR complex in heterodimeric $\alpha\beta$ form includes eight chains, namely an alpha chain (referred to herein as TCR$\alpha$ or TCR alpha), beta chain (referred to herein as TCR$\beta$ or TCR beta), delta chain, gamma chain, two epsilon chains and two zeta chains. The alpha and beta TCR chains include variable (V) and constant (C) regions. TCR diversity is generated from genetic recombination (VJ recombination of alpha chains and VDJ recombination of beta chains) resulting in areas of intersection that are important for antigen (i.e., peptide/MHC) recognition.

In some instances, a TCR repertoire library may include TCR-$\alpha$ chain sequences, TCR-$\beta$ chain sequences, or both TCR-$\alpha$ chain sequences and TCR-$\beta$ chain sequences. TCR chain sequences of a subject TCR repertoire library may include full length TCR chain sequences (e.g., full length TCR alpha chain sequences, full length TCR beta chain sequences) or partial TCR chain sequences (e.g., partial length TCR alpha chain sequences, partial length TCR beta chain sequences).

Where the subject TCR repertoire library members include partial TCR chain sequences, the partial TCR chain sequences may include the entire or essentially the entire TCR chain variable region (e.g., the TCR alpha chain variable region, the TCR beta chain variable region). In some instances, the resulting library members include the TCR variable region and at least a portion of the TCR constant region. In some instances, the resulting library members include sequence corresponding to the TCR alpha and/or beta chain 5' mRNA ends. In some instances, the resulting library members include sequence from the TCR alpha or beta chain 5' end to at least a portion of the corresponding chain constant region.

In certain embodiments, preparation of the immune cell specific library may include TCR specific amplification. Such TCR specific amplification may make use of a TCR specific primer. By "TCR specific primer" is meant a primer that specifically hybridizes to a region of a TCR chain (e.g., a TCR alpha chain, a TCR beta chain) nucleic acid sequence or the complement thereof. In some instances, a TCR specific primer may hybridize to only one type of TCR chain, e.g., only a TCR alpha chain or only a TCR beta chain. In some instances, a TCR specific primer may be configured to hybridize to more than one type of TCR chain, e.g., configured to hybridize to both a TCR alpha chain and a TCR beta chain.

TCR specific primers may be designed to specifically hybridize to a TCR alpha chain constant region or the complement thereof. For example, in some instances, a TCR specific primer may hybridize to a mammalian TCR alpha chain constant region or a complement thereof, including e.g., a human TCR alpha chain constant region, a mouse TCR alpha chain constant region, or the like.

An exemplary human TCR alpha chain constant region has the following amino acid sequence:

(SEQ ID NO: 07)
PNIQNPDPAVYQLRDSKSSDKSVCLFTDFDSQTNVSQSKDSDVYITDKTV
LDMRSMDFKSNSAVAWSNKSDFACANAFNNSIIPEDTFFPSPESSCDVKL
VEKSFETDTNLNFQNLSVIGFRILLLKVAGFNLLMTLRLWSS, which is encoded by the following nucleic acid sequence:

CCAAATATCCAGAACCCTGACCCTGCCGTGTACCAGCTGAGAGACTCTAA
ATCCAGTGACAAGTCTGTCTGCCTATTCACCGATTTTGATTCTCAAACAA
ATGTGTCACAAAGTAAGGATTCTGATGTGTATATCACAGACAAAACTGTG
CTAGACATGAGGTCTATGGACTTCAAGAGCAACAGTGCTGTGGCCTGGAG
CAACAAATCTGACTTTGCATGTGCAAACGCCTTCAACAACAGCATTATTC
CAGAAGACACCTTCTTCCCCAGCCCAGAAAGTTCCTGTGATGTCAAGCTG
GTCGAGAAAAGCTTTGAAACAGATACGAACCTAAACTTTCAAAACCTGTC
AGTGATTGGGTTCCGAATCCTCCTCCTGAAAGTGGCCGGGTTTAATCTGC
TCATGACGCTGCGGCTGTGGTCCAGCTGA (SEQ ID NO: 08; T-
cell receptor alpha chain C region, human; GenBank:
AY247834.1, AAO72258.1; UniProtKB: P01848).

An exemplary mouse TCR alpha chain constant region has the following amino acid sequence:

PYIQNPEPAVYQLKDPRSQDSTLCLFTDFDSQINVPKTMESGTFITDKTV
LDMKAMDSKSNGAIAWSNQTSFTCQDIFKETNATYPSSDVPCDATLTEKS
FETDMNLNFQNLSVMGLRILLLKVAGFNLLMTLRLWSS (SEQ ID
NO: 09; UniProtKB: P01849)
or
PNIQNPEPAVYQLKDPRSQDSTLCLFTDFDSQINVPKTMESGTFITDKTV
LDMKAMDSKSNGAIAWSNQTSFTCQDIFKETNATYPSSDVPCDATLTEKS
FETDMNLNFQNLSVMGLRILLLKVAGFNLLMTLRLWSS (SEQ ID
NO: 10; GenBank: AAA53226.1)

which are encoded by the following nucleic acid sequences, respectively:

(SEQ ID NO: 11)
CCATACATCCAGAACCCAGAACCTGCTGTGTACCAGTTAAAAGATCCTCG
GTCTCAGGACAGCACCCTCTGCCTGTTCACCGACTTTGACTCCCAAATCA
ATGTGCCGAAAACCATGGAATCTGGAACGTTCATCACTGACAAAACTGTG
CTGGACATGAAAGCTATGGATTCCAAGAGCAATGGGGCCATTGCCTGGAG
CAACCAGACAAGCTTCACCTGCCAAGATATCTTCAAAGAGACCAACGCCA
CCTACCCCAGTTCAGACGTTCCCTGTGATGCCACGTTGACCGAGAAAAGC
TTTGAAACAGATATGAACCTAAACTTTCAAAACCTGTCAGTTATGGGACT
CCGAATCCTCCTGCTGAAAGTAGCGGGATTTAACCTGCTCATGACGCTGA
GGCTGTGGTCCAGT,

CCAAACATCCAGAACCCAGAACCTGCTGTGTACCAGTTAAAAGATCCTCG
GTCTCAGGACAGCACCCTCTGCCTGTTCACCGACTTTGACTCCCAAATCA
ATGTGCCGAAAACCATGGAATCTGGAACGTTCATCACTGACAAAACTGTG
CTGGACATGAAAGCTATGGATTCCAAGAGCAATGGGGCCATTGCCTGGAG
CAACCAGACAAGCTTCACCTGCCAAGATATCTTCAAAGAGACCAACGCCA
CCTACCCCAGTTCAGACGTTCCCTGTGATGCCACGTTGACCGAGAAAAGC
TTTGAAACAGATATGAACCTAAACTTTCAAAACCTGTCAGTTATGGGACT
CCGAATCCTCCTGCTGAAAGTAGCGGGATTTAACCTGCTCATGACGCTGA
GGCTGTGGTCCAGT (SEQ ID NO: 12; GenBank: U07662.1).

TCR specific primers may be designed to specifically hybridize to a TCR beta chain (e.g., a TCR beta 1 chain constant region or a TCR beta 2 chain constant region) constant region or the complement thereof. For example, in some instances, a TCR specific primer may hybridize to a mammalian TCR beta chain constant region or a complement thereof, including e.g., a human TCR beta chain constant region, a mouse TCR beta chain constant region, or the like.

An exemplary human TCR beta chain 1 constant region has the following amino acid sequence:

EDLNKVFPPEVAVFEPSEAEISHTQKATLVCLATGFFPDHVELSWWVNGK
EVHSGVSTDPQPLKEQPALNDSRYCLSSRLRVSATFWQNPRNHFRCQVQF
YGLSENDEWTQDRAKPVTQIVSAEAWGRADCGFTSVSYQQGVLSATILYE
ILLGKATLYAVLVSALVLMAMVKRKDF (SEQ ID NO: 13; Uni-
ProtKB: P01850; GenBank: CAA25134.1)

which is encoded by the following nucleic acid sequence:

GAGGACCTGAACAAGGTGTTCCCACCCGAGGTCGCTGTGTTTGAGCCATCA
GAAGCAGAGATCTCCCACACCCAAAAGGCCACACTGGTGTGCCTGGCCACA
GGCTTCTTCCCCGACCACGTGGAGCTGAGCTGGTGGGTGAATGGGAAGGAG
GTGCACAGTGGGGTCAGCACAGACCCGCAGCCCCTCAAGGAGCAGCCCGCC
CTCAATGACTCCAGATACTGCCTGAGCAGCCGCCTGAGGGTCTCGGCCACC
TTCTGGCAGAACCCCCGCAACCACTTCCGCTGTCAAGTCCAGTTCTACGGG
CTCTCGGAGAATGACGAGTGGACCCAGGATAGGGCCAAACCCGTCACCCAG
ATCGTCAGCGCCGAGGCCTGGGGTAGAGCAGACTGTGGCTTTACCTCGGTG
TCCTACCAGCAAGGGGTCCTGTCTGCCACCATCCTCTATGAGATCCTGCTA
GGGAAGGCCACCCTGTATGCTGTGCTGGTCAGCGCCCTTGTGTTGATGGCC
ATGGTCAAGAGAAAGGATTTC (SEQ ID NO: 14; GenBank:
EF101778.1, X00437.1).

An exemplary human TCR beta chain 2 constant region has the following amino acid sequence:

DLKNVFPPEVAVFEPSEAEISHTQKATLVCLATGFYPDHVELSWWVNGKE
VHSGVSTDPQPLKEQPALNDSRYCLSSRLRVSATFWQNPRNHFRCQVQFY
GLSENDEWTQDRAKPVTQIVSAEAWGRADCGFTSESYQQGVLSATILYEI
LLGKATLYAVLVSALVLMAMVKRKDSRG (SEQ ID NO: 15; UniProtKB: A0A5B9, GenBank: AAA60662.1)

which is encoded by the following nucleic acid sequence:

GACCTGAAAAACGTGTTCCCACCCGAGGTCGCTGTGTTTGAGCCATCAGA
AGCAGAGATCTCCCACACCCAAAAGGCCACACTGGTATGCCTGGCCACAG
GCTTCTACCCCGACCACGTGGAGCTGAGCTGGTGGGTGAATGGGAAGGAG
GTGCACAGTGGGGTCAGCACAGACCCGCAGCCCCTCAAGGAGCAGCCCGC
CCTCAATGACTCCAGATACTGCCTGAGCAGCCGCCTGAGGGTCTCGGCCA
CCTTCTGGCAGAACCCCCGCAACCACTTCCGCTGTCAAGTCCAGTTCTAC
GGGCTCTCGGAGAATGACGAGTGGACCCAGGATAGGGCCAAACCCGTCAC
CCAGATCGTCAGCGCCGAGGCCTGGGGTAGAGCAGACTGTGGCTTCACCT
CCGAGTCTTACCAGCAAGGGGTCCTGTCTGCCACCATCCTCTATGAGATC
TTGCTAGGGAAGGCCACCTTGTATGCCGTGCTGGTCAGTGCCCTCGTGCT
GATGGCCATGGTCAAGAGAAAGGATTCCAGAGGCTAG (SEQ ID NO: 16; GenBank: L34740.1).

An exemplary mouse TCR beta chain 1 constant region has the following amino acid sequence:

EDLRNVTPPKVSLFEPSKAEIANKQKATLVCLARGFFPDHVELSWWVNGK
EVHSGVSTDPQAYKESNYSYCLSSRLRVSATFWHNPRNHFRCQVQFHGLS
EEDKWPEGSPKPVTQNISAEAWGRADCGITSASYQQGVLSATILYEILLG
KATLYAVLVSTLVVMAMVKRKNS (SEQ ID NO: 17; UniProtKB: P01852)

which is encoded by the following nucleic acid sequence:
GAGGATCTGAGAAATGTGACTCCACCCAAGGTCTCCTTGTTTGAGCCATC
AAAAGCAGAGATTGCAAACAAACAAAAGGCTACCCTCGTGTGCTTGGCCA
GGGGCTTCTTCCCTGACCACGTGGAGCTGAGCTGGTGGGTGAATGGCAAG
GAGGTCCACAGTGGGGTCAGCACGGACCCTCAGGCCTACAAGGAGAGCAA
TTATAGCTACTGCCTGAGCAGCCGCCTGAGGGTCTCTGCTACCTTCTGGC
ACAATCCTCGCAACCACTTCCGCTGCCAAGTGCAGTTCCATGGGCTTTCA
GAGGAGGACAAGTGGCCAGAGGGCTCACCCAAACCTGTCACACAGAACAT
CAGTGCAGAGGCCTGGGGCCGAGCAGACTGTGGGATTACCTCAGCATCCT
ATCAACAAGGGGTCTTGTCTGCCACCATCCTCTATGAGATCCTGCTAGGG
AAAGCCACCCTGTATGCTGTGCTTGTCAGTACACTGGTGGTGATGGCTAT
GGTCAAAAGAAAGAATTCATGA (SEQ ID NO: 18; GenBank: FJ188408.1).

An exemplary mouse TCR beta chain 2 constant region has the following amino acid sequence:

EDLRNVTPPKVSLFEPSKAEIANKQKATLVCLARGFFPDHVELSWWVNGK
EVHSGVSTDPQAYKESNYSYCLSSRLRVSATFWHNPRNHFRCQVQFHGLS
EEDKWPEGSPKPVTQNISAEAWGRADCGITSASYHQGVLSATILYEILLG
KATLYAVLVSGLVLMAMVKKKNS (SEQ ID NO: 19; UniProtKB: P01851)

which is encoded by the following nucleic acid sequence:

GAGGATCTGAGAAATGTGACTCCACCCAAGGTCTCCTTGTTTGAGCCATC
AAAAGCAGAGATTGCAAACAAACAAAAGGCTACCCTCGTGTGCTTGGCCA
GGGGCTTCTTCCCTGACCACGTGGAGCTGAGCTGGTGGGTGAATGGCAAG
GAGGTCCACAGTGGGGTCAGCACGGACCCTCAGGCCTACAAGGAGAGCAA
TTATAGCTACTGCCTGAGCAGCCGCCTGAGGGTCTCTGCTACCTTCTGGC
ACAATCCTCGAAACCACTTCCGCTGCCAAGTGCAGTTCCATGGGCTTTCA
GAGGAGGACAAGTGGCCAGAGGGCTCACCCAAACCTGTCACACAGAACAT
CAGTGCAGAGGCCTGGGGCCGAGCAGACTGTGGAATCACTTCAGCATCCT
ATCATCAGGGGGTTCTGTCTGCAACCATCCTCTATGAGATCCTACTGGGG
AAGGCCACCCTATATGCTGTGCTGGTCAGTGGCCTGGTGCTGATGGCCAT
GGTCAAGAAAAAAAATTCCTGA (SEQ ID NO: 20; GenBank: U46841.1).

In some instances, an immune cell receptor repertoire library may include a BCR repertoire library. The BCR complex is found on the surface of B cells and includes a membrane bound immunoglobulin (i.e., antibody) binding moiety, which includes a heavy and a light chain, each of which contains a constant (C) and a variable (V) region. The immunoglobulin chain of the BCR is bound by disulfide bridges to a signal transducing CD79A/B chains. The immunoglobulin chains of the BCR may be of various isotypes including IgD, IgM, IgA, IgG or IgE. Similar to the TCR, the immunoglobulin portion of the BCR undergoes V(D)J recombination to generate enormous diversity within a population.

In some instances, an immune cell receptor repertoire library may include a BCR repertoire library, where e.g., the BCR repertoire library may include BCR immunoglobulin chain sequences (including e.g., IgD, IgM, IgA, IgG or IgE chain sequences). Immunoglobulin chain sequences of a subject BCR repertoire library may include full length immunoglobulin chain sequences (e.g., full length heavy chain sequences, full length light chain sequences) or partial immunoglobulin sequences (e.g., partial heavy chain sequences, partial light chain sequences).

Where the subject BCR repertoire library members include partial immunoglobulin chain sequences, the partial immunoglobulin chain sequences may include the entire or essentially the entire immunoglobulin variable region (e.g., the immunoglobulin light chain variable region(s), the immunoglobulin heavy chain variable region(s)). In some instances, the resulting library members include the immunoglobulin variable region(s) and at least a portion of an immunoglobulin constant region. In some instances, the resulting library members include sequence corresponding to the immunoglobulin heavy and/or light chain 5' mRNA ends. In some instances, the resulting library members include sequence from the immunoglobulin heavy or light chain 5' end to at least a portion of the corresponding immunoglobulin chain constant region.

In certain embodiments, preparation of the immune cell specific library may include BCR specific amplification (including e.g., immunoglobulin chain specific amplification). Such immunoglobulin specific amplification may make use of an immunoglobulin specific primer. By "immunoglobulin specific primer" is meant a primer that specifically hybridizes to a region of an immunoglobulin chain (e.g., a immunoglobulin heavy chain, an immunoglobulin light chain) nucleic acid sequence or the complement thereof. In some instances, an immunoglobulin specific primer may hybridize to only one type of immunoglobulin chain, e.g., only an immunoglobulin heavy chain, only an immunoglobulin light chain, only an IgD chain, only an IgM chain, only an IgA chain, only an IgG chain, only an IgE chain, etc.

Immunoglobulin specific primers may be designed to specifically hybridize to an immunoglobulin heavy chain constant region or the complement thereof. For example, in some instances, an immunoglobulin specific primer may hybridize to a mammalian immunoglobulin heavy chain constant region or a complement thereof, including e.g., a human immunoglobulin heavy chain constant region, a mouse immunoglobulin heavy chain constant region, or the like.

Immunoglobulin specific primers may be designed to specifically hybridize to an immunoglobulin light chain constant region or the complement thereof. For example, in some instances, an immunoglobulin specific primer may hybridize to a mammalian immunoglobulin light chain constant region or a complement thereof, including e.g., a human immunoglobulin light chain constant region, a mouse immunoglobulin light chain constant region, or the like.

Amplification performed during library preparation, including e.g., immune receptor specific amplification, may be performed in a single round or multiple rounds of amplification may be employed. For example, in some instances, after a first round of amplification one or more amplification primers not utilized in the first round, e.g., a second pair of blocked amplification (e.g., as described above) may be unblocked to facilitate a second round of amplification using the product of the first round of amplification as a nucleic acid template. In some instances, the second or subsequent round(s) of amplification may involve nested amplification, i.e., where the primer binding sites utilized in the second or subsequent round(s) of amplification are within (i.e., one or more nucleotides from the 3' or 5' end) of the product generated in the first round of amplification. Where employed, the degree of nesting will vary as desired including e.g., where the second or subsequent primer binding site is one or more, including 2 or more, 3 or more, 4 or more, 5 or more, 6 or more, 7 or more, 8 or more, 9 or more, 10 or more, 15 or more, 20 or more, etc., nucleotides from the 3' or 5' end of the amplicon generated in the first round of amplification.

In some instances, second or subsequent round(s) amplification will not be nested, including where the second round of amplification makes use of one or more primer binding sites utilized in the prior round of amplification or a primer binding site added during the prior round of amplification (e.g., a primer binding site added as part of a non-templated sequence). In some instances, a second or subsequent round of amplification may make use of a nested primer amplification site at one end and a non-nested (e.g., a prior used primer binding site or an added primer binding site) at the other end, including where the nested site is at the 3' end of the amplicon or the 5' end of the amplicon.

Following prescribed library amplification steps, the prepared libraries may be considered ready for sequencing. In certain embodiments, the methods provided may further include subjecting a prepared immune cell receptor repertoire library to an NGS protocol. The protocol may be carried out on any suitable NGS sequencing platform. NGS sequencing platforms of interest include, but are not limited to, a sequencing platform provided by Illumina® (e.g., the HiSeq™, MiSeq™ and/or NextSeq™ sequencing systems); Ion Torrent™ (e.g., the Ion PGM™ and/or Ion Proton™ sequencing systems); Pacific Biosciences (e.g., the PACBIO RS II Sequel sequencing system); Life Technologies™ (e.g., a SOLiD sequencing system); Roche (e.g., the 454 GS FLX+ and/or GS Junior sequencing systems); or any other sequencing platform of interest. The NGS protocol will vary depending on the particular NGS sequencing system employed. Detailed protocols for sequencing an NGS library, e.g., which may include further amplification (e.g., solid-phase amplification), sequencing the amplicons, and analyzing the sequencing data are available from the manufacturer of the NGS sequencing system employed.

B. Blocked Primer Pair Amplification

Provided herein are methods for amplifying selected target sequences (e.g., mRNA sequences) using a first primer pair that is blocked with thermo-labile moieties and a second primer pair blocked with enzyme-labile moieties. In certain embodiments, such methods are employed with T-cells to amplify and estimate TCR a/b diversity. Such methods are exemplified in the context of T-cell receptor amplification below.

In certain embodiments, the methods disclosed here are used to examine the TCR a/b diversity in live, single cells on-chip with an optimized dispense process (e.g., utilizing the WAFERGEN ICELL8 system). In certain embodiments, the methods disclosed herein allow one to consolidate the number of reagent additions using methods known in the art, such as Takara Bio USA TCR amplification kits (Takara Bio USA Cat. Nos. 635014, 635015, 635016), shown in FIG. 1), so that the total number of reagent handling steps (e.g., by a user or an automated device) is reduced to three dispenses (including the cells at single-cell concentration). In addition to the dispense steps performed, in certain embodiments, a number of the reagents are pre-printed in the wells of a multi-well device (e.g., the second primer pair that has 3' blocked ends that are enzyme cleavable). In certain embodiments, the first and second blocked primer pairs provide both well-specific barcodes and UMI's utilizing a dual-indexed, pair-end sequencing strategy.

Figure 2:
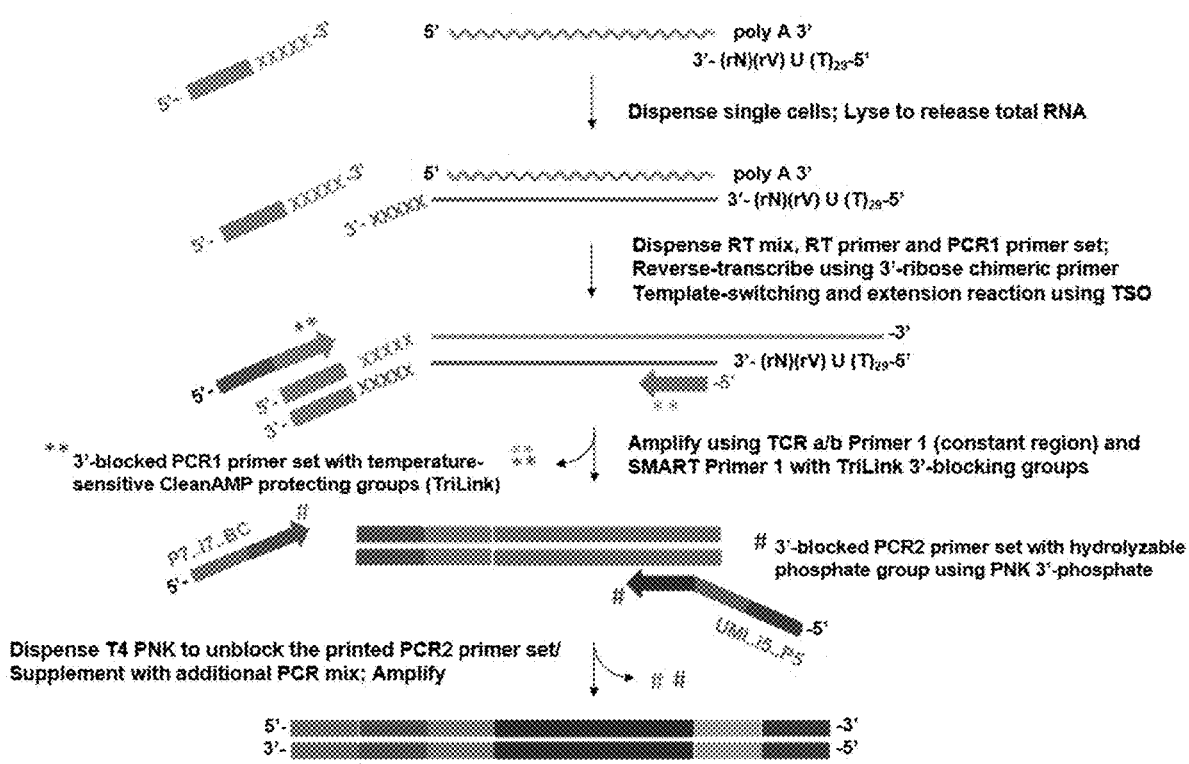
FIG. 2 shows an exemplary workflow of one embodiment of the present disclosure, showing the workflow with a 3'-ribose RT primer and two sets of 3'-blocked PCR primers (PCR1 and PCR2).
Figure 3:
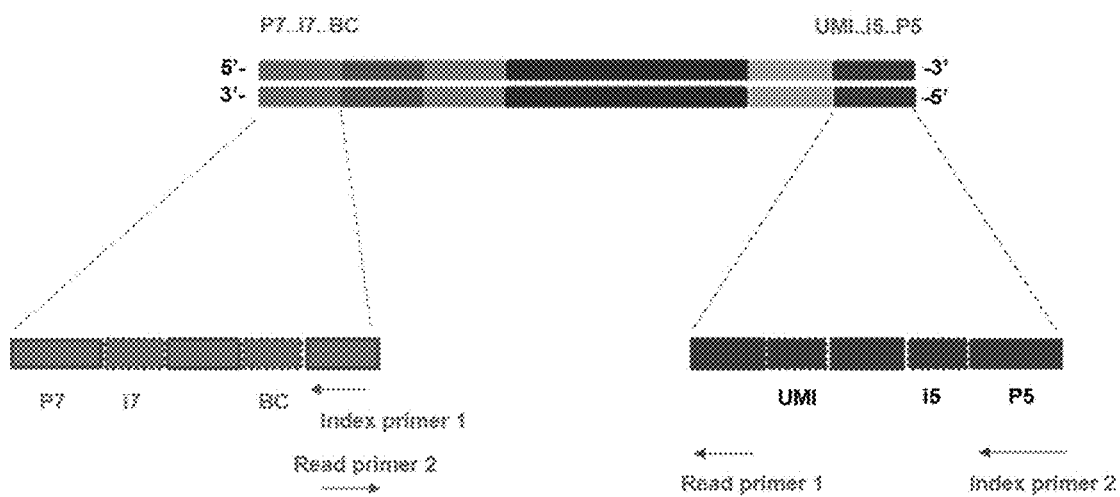
FIG. 3 shows an exemplary result of amplification with two sets of 3' blocked PCR primers, wherein the amplified sequences are dual indexed, paired end libraries with well-specific barcodes and Unique Molecular Identifiers (UMI's).

Exemplary embodiments include those shown in FIG. 2. The methodology shown in FIG. 2 can be used on a multi-well device that contains 5184 wells. The blocked second primer pair (PCR2 primers; with 3' blocked, enzyme cleavable ends) can be pre-printed in the wells, with seventy-two upstream PCR2 primers with well-specific barcode/i7+P7 in x-orientation, and seventy-two downstream PCR2 primers with UMI's/i5+P5 in y-orientation (see also FIG. 3). One can dispense the T-cells into the wells as a single-cell concentration (see, e.g., Poisson dispensing further below). Then, one can dispense the reverse transcriptase (RT) mix with Oligo-dT primer and the first blocked primer pair (PCR1) primer set (with thermolabile 3' blocked ends). The wells can then be incubated for the RT reaction (to generate first strand cDNA), and then thermocycling can be employed to denature the RT and activate the PCR1 primer set (e.g., such that increased heat causes the 3' blocked ends to come off the first primer pair). The first primer pair, along with the thermostable polymerase, can then generate amplification products. One can then dispense an enzyme to remove the 3' block on the second primer pair (e.g., T4 PNK), and concurrently add additional PCR mix to supplement if necessary. In certain embodiments, this workflow is optimized and adapted for use on the ICELL8 single-cell system from WAFERGEN.

In certain embodiments, a modified oligo(dT) primer with two or three (or more) ribonucleotides at 3' end is used in the RT step to prevent incorporation during subsequent PCR steps. For example, Taq polymerases show very little ability to extend off an RNA primer containing more than one ribonucleotide at 3' end, and therefore Taq or a similar enzyme is used for PCR in following steps. In some embodiments, the 3' blocked PCR1 primer set has incorporated nucleotides having the temperature-sensitive CleanAmp protecting group (TriLink). This protecting group is gradually released with each successive 95 degree Celsius denaturation step in a typical PCR amplification reaction using standard Taq polymerase. Thus, the first PCR amplification is delayed until the reverse transcription reaction is complete and the RTase (e.g., MMLV) is inactivated. In certain embodiments, the 3' blocked PCR2 primer set has 3'-phosphate groups. These oligos cannot participate in the semi-nested PCR until the 3'-phosphate block on this DNA oligo is removed by, for example, T4 PNK's 3' phosphatase activity.

Figure 5:
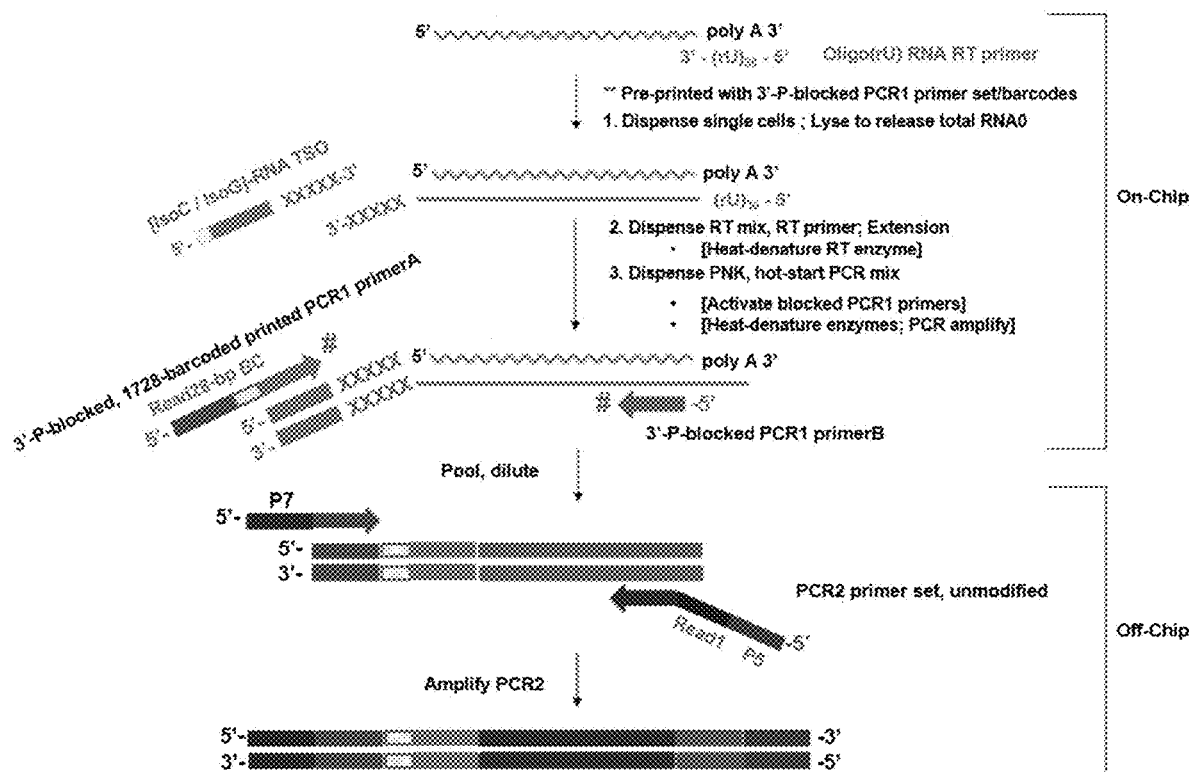
FIG. 5 shows an exemplary workflow of one embodiment of the present disclosure, showing the workflow with a 3'-ribose RT primer, a TSO oligo with IsoC and/or IsoG nucleotides, a 3'-blocked first primer pair, and second primer pair with P7 and P5 sequencing adapter sequences.

In other embodiments, provided herein are methods of amplifying RNA from a sample using a 3'-ribose RT primer, a TSO oligo with IsoC and/or IsoG nucleotides, a 3'-blocked first primer pair, and second primer pair with sequencing adapter sequences. There is generally a large expense with putting a barcode on a chimeric RNA/DNA template-switching oligo that also incorporates non-natural bases (e.g., IsoC/IsoG; to prevent concatamerization during RT step). The disclosed method allows the use of IsoC/IsoG in a template switching oligonucleotide (e.g., as shown in FIG. 5), such that the barcode sequence can be one the one of the primers in the first primer pair (as shown in FIG. 5). As shown in FIG. 5, the PCR1 reaction may be performed in a multi-well device (e.g., a multi-well chip), using pre-printed primers, which are de-blocked (e.g., using PNK) prior to the first PCR cycle. In certain embodiments, the second primer pair is not performed in the multi-well device (e.g., chip), but instead, is performed completely off-chip.

C. Poisson Dispensing

In certain embodiments, the blocked primer pair methods (e.g., disclosed in FIGS. 2 and 5) and systems disclosed herein employ a method that allows a certain number of cells to be present in cell suspension (if intact cells are used) that are dispensed into the well or wells, such that the average over many such dispenses results in a single cell being dispensed in a given well. A statistical description of this phenomenon is known as the Poisson distribution. In theory, dispensing a single cell per well (n=exactly 1 cell, but not 0, 2, 3, 4, 5, 6 etc. cells) is constrained by theta theoretical maxima=of 36.8% of wells will contain exactly 1 cell. However, the Poisson distribution however can be leveraged to alter the input cell concentration to a very wide range of occupancy rates. Methods for achieving a Poisson distribution are described in U.S. patent application Ser. No. 15/049, 056, which application is herein incorporated by reference in its entirety. As described in that application, a source of cells is diluted using Poisson statistics such that on average 1 cell per dispense volume is dispensed. In certain embodiments, microscopy (e.g., magnifying optics) is used to visualize each well and directly know if that well contains a single cell (e.g., prior to lysing the cell to release the RNA and performing the blocker primer pair methods described herein). In certain embodiments, multi-sample dispensers (e.g., from WAFERGEN) are programmed to perform a variety series of biochemical steps including lysis, and the addition of reagents for the blocker primer pair methods disclosed herein.

In certain embodiments, when wells are identified as having received zero cells, a second (and third) optional Recursive Poisson Distribution (RPD) step may be employed to circumvent the statistical limitations of the Poisson distribution, thereby raising single cell occupancy rates on-chip from a theoretical maxima of 37% to >50%. The RPD in this disclosure refers to the iterative cycle of, (a) dispensing cell-containing solutions into reaction vessels (wells, chambers, etc.) in a chip, (b) visualization of cells on-chip in individual wells, (c) identifying the on-chip cell counts (equal to zero, equal to one, and greater than one) in individual wells by software-aided microscopy, and, (d) performing additional dispense cycles of cell-containing solutions into individual wells specifically identified in the previous round as having a cell count of zero. The objective of RPD is to maximize the number of occupied reaction vessels (wells, chambers, etc.) containing a single-cell (or some other desired number of cells) above the theoretical limitations Poisson distribution for a single dispense. This disclosure does not place a limit on the number of iterative cycles.

D. Cells

The present disclosure is not limited by the type of cells that are employed in the blocked primer pair methods. In certain embodiments, T-cells (e.g., human T-cells), cancer cells, circulating cancer cells, stem cells, and cancer stem cells are employed. Most cancer deaths appear to be caused by metastatic spread and growth by circulating tumor cells at distant organs. Circulating tumor cells (CTCs), CTC clusters (two or more individual CTCs bound together), and cancer stem cells (CSCs) may be initially localized, latent systemic, or post-adjuvant treatment depleted. Consequently, CTCs and the relevant stem cells are frequently present at low numbers within a large background of normal non-cancerous cells. The low frequency of these cells generates a complex "needle in a haystack" analysis problem for detecting the required cancer cell signal within the large 'noise" background. Detection of cancer cell specific cell surface markers and analysis of these cells is deeply relevant to understanding the biology of metastatic spread. The methods and systems provided herein allow isolation and analysis of such important cancer cells.

Single-cell, multiple-cell and cell clusters may initially be either enriched or depleted from a cell or tissue milieu or population, based on the presence of antigenic/phenotypic cell-surface or intra-cellular markers including but not restricted to: protein, lipid, carbohydrate (i.e. glycosylation) post-translational modifications of those moieties, nucleic acids and their modifications, or varying combinations of these moieties. Detection of cell surface markers in single cells—including cancer cells—and transferring those cells into discrete individual wells of a microfluidic device (e.g., Wafergen's SmartChip wells) is performed with the methods and systems described herein. In other embodiments, labelled cells may be dispensed directly into wells and antigenic moieties detected directly in chip via standard or automated microscopy using a variety of widely available fluorescence filters.

Methods of circulating tumor cell (CTC) enrichment and visualization are known in the art and may be employed for generating (and later visualizing) the initial cell suspension employed in the methods and systems described herein. For example, Table 1 of Krebs et al. Nat Rev Clin Oncol. 2014 March; 11(3):129-44 (herein incorporated by reference, and specifically with respect to Table 1). Examples of markers that can be employed to enrich and visualize CTCs include, but are not limited to: CD45, EpCAM, MUC1, and HER2. Antibodies to such markers may be employed to label and visualize such cells. Any type of suitable method may be employed for isolating and enriching CTCs, such as flow cytometry, column binding, etc.

In certain embodiments, the cells that are examined are T-cells, and at least one pair of primers are specific for amplifying alpha and beta T-cell receptors present in the T-cells. One aspect of cellular adaptive immunity is mediated by T-cells, a class of lymphocytes with specialized extracellular receptors (T-cell receptors or TCR's). These TCR's selectively bind antigens from pathogens that have been presented by a different type of immune cell (APC's). A tremendous repertoire diversity of TCR's is required to encompass all of the specific antigen-binding possibilities. This diversity is achieved by V(D)J recombination and the resulting T-cell clonal population has a "clonotype" consisting of a particular pairing of TCR variants (TCRα and TCRβ subunits). The Takara Bio USA SMARTer Human TCR a/b Profiling Kit (Clontech Cat. Nos. 635014, 635015, 635016; herein incorporated by reference) is a methodology for TCR mRNA profiling. The kit utilizes a template-switching methodology (SMART; Switching Mechanism at the 5' end of RNA Template) and semi-nested PCR to reverse-transcribe and amplify variable regions of TCRα and TCRβ subunit from total RNA. These kits can be modified as described herein to employ the blocker primer pairs and non-extendable (by certain polymerases) RNA primers described herein.

E. Multi-Well Device

In certain embodiments, the reaction vessel employed is a well or wells of a multi-well device. The present disclosure is not limited by the type of multi-well testing devices (e.g., plates or chips) employed. In general, such devices have a plurality of wells that contain, or are dimensioned to contain, liquid (e.g., liquid that is trapped in the wells such that gravity alone cannot make the liquid flow out of the wells). One exemplary chip is WAFERGEN's 5184-well SMARTCHIP. Other exemplary chips are provided in U.S. Pat. Nos. 8,252,581; 7,833,709; and 7,547,556, all of which are herein incorporated by reference in their entireties including, for example, for the teaching of chips, wells, thermocycling conditions, and associated reagents used therein). Other exemplary chips include the OPENARRAY plates used in the QUANTSTUDIO real-time PCR system (Applied Biosystems). Another exemplary multi-well device is a 96-well or 384-well plate.

The overall size of the multi-well devices may vary and it can range, for example, from a few microns to a few centimeters in thickness, and from a few millimeters to 50 centimeters in width or length. Typically, the size of the entire device ranges from about 10 mm to about 200 mm in width and/or length, and about 1 mm to about 10 mm in thickness. In some embodiments, the chip is about 40 mm in width by 40 mm in length by 3 mm in thickness.

The total number of wells (e.g., nanowells) on the multi-well device may vary depending on the particular application in which the subject chips are to be employed. The density of the wells on the chip surface may vary depending on the particular application. The density of wells, and the size and volume of wells, may vary depending on the desired application and such factors as, for example, the species of the organism for which the methods of this disclosure are to be employed.

The present disclosure is not limited by the number of wells in the multi-well device or the number of wells in the multi-well source device. A large number of wells may be incorporated into a device. In various embodiments, the total number of wells on the device is from about 100 to about 200,000, or from about 5000 to about 10,000. In other embodiments the device comprises smaller chips, each of which comprises about 5,000 to about 20,000 wells. For example, a square chip may comprise 125 by 125 nanowells, with a diameter of 0.1 mm.

The wells (e.g., nanowells) in the multi-well devices may be fabricated in any convenient size, shape or volume. The well may be about 100 µm to about 1 mm in length, about 100 µm to about 1 mm in width, and about 100 µm to about 1 mm in depth. In various embodiments, each nanowell has an aspect ratio (ratio of depth to width) of from about 1 to about 4. In one embodiment, each nanowell has an aspect ratio of about 2. The transverse sectional area may be circular, elliptical, oval, conical, rectangular, triangular, polyhedral, or in any other shape. The transverse area at any given depth of the well may also vary in size and shape.

In certain embodiments, the wells have a volume of from 0.1 nl to 1 µl. The nanowell may have a volume of 1 µl or less, such as 500 nl or less. The volume may be 200 nl or less, including 100 nl or less. In an embodiment, the volume of the nanowell is 100 nl. Where desired, the nanowell can be fabricated to increase the surface area to volume ratio, thereby facilitating heat transfer through the unit, which can reduce the ramp time of a thermal cycle. The cavity of each well (e.g., nanowell) may take a variety of configurations. For instance, the cavity within a well may be divided by linear or curved walls to form separate but adjacent compartments, or by circular walls to form inner and outer annular compartments.

A well of high inner surface to volume ratio may be coated with materials to reduce the possibility that the reactants contained therein may interact with the inner surfaces of the well if this is desired. Coating is particularly useful if the reagents are prone to interact or adhere to the inner surfaces undesirably. Depending on the properties of the reactants, hydrophobic or hydrophilic coatings may be selected. A variety of appropriate coating materials are available in the art. Some of the materials may covalently adhere to the surface, others may attach to the surface via non-covalent interactions. Non-limiting examples of coating materials include silanization reagent such as dimethychlorosilane, dimethydichlorosilane, hexamethyldisilazane or trimethylchlorosilane, polymaleimide, and siliconizing reagents such as silicon oxide, AQUASIL™ siliconizing reagents, and SURFASIL™ siliconizing reagents. Additional suitable coating materials are blocking agents such as amino acids, or polymers including but not limited to polyvinylpyrrolidone, polyadenylic acid and polymaleimide. Certain coating materials can be cross-linked to the surface via heating, radiation, and by chemical reactions. Those skilled in the art will know of other suitable means for coating a nanowell of a multi-well device, or will be able to ascertain such, without undue experimentation.

An exemplary multi-well device (e.g., chip) may have a thickness of about 0.625 mm, with a well have having dimensions of about 0.25 mm (250 um) in length and width. The nanowell depth can be about 0.525 mm (525 um), leaving about 0.1 mm of the chip beneath a given well. A nanowell opening can include any shape, such as round, square, rectangle or any other desired geometric shape. By way of example, a nanowell can include a diameter or width of between about 100 µm and about 1 mm, a pitch or length of between about 150 µm and about 1 mm and a depth of between about 10 µm to about 1 mm. The cavity of each well may take a variety of configurations. For instance, the cavity within a nanowell may be divided by linear or curved walls to form separate but adjacent compartments.

The wells (e.g., nanowells) of the multi-well device may be formed using, for example, commonly known photolithography techniques. The nanowells may be formed using a wet KOH etching technique, an anisotropic dry etching technique, mechanical drilling, injection molding and or thermo forming (e.g., hot embossing).

F. Dual-Axis Barcode Systems

In some embodiments, provided herein is an X/Y barcode scheme (e.g., methods, systems, compositions, etc.) in which each column (X) and row (Y) of a multi-well array is identified by a unique barcode. In such embodiments, the first and/or second blocked primer pairs are provided with the suitable column and row barcodes such that individual wells may be identified based on the combination of X and Y barcodes. Using such a scheme, each individual well is identified by a unique barcode identifier signifying its column and row in the array. In some embodiments, this system allows unique identifiers applied to nucleic acids within the wells, while minimizing the number of barcoded primers required. For example, 144 barcodes (72 X barcodes and 72 Y barcodes) allow for unique identification of 5184 wells on a 72×72 array (e.g., SMARTCHIP by Wafergen).

In some embodiments, in addition to the X/Y barcodes, nucleic acids may be labeled (e.g., via reverse transcription, amplification, template switching, etc.) with one or more of: a unique molecular identifier sequence (e.g., a molecule specific tag), one or more sequencing sequences, etc.

Figure 4:
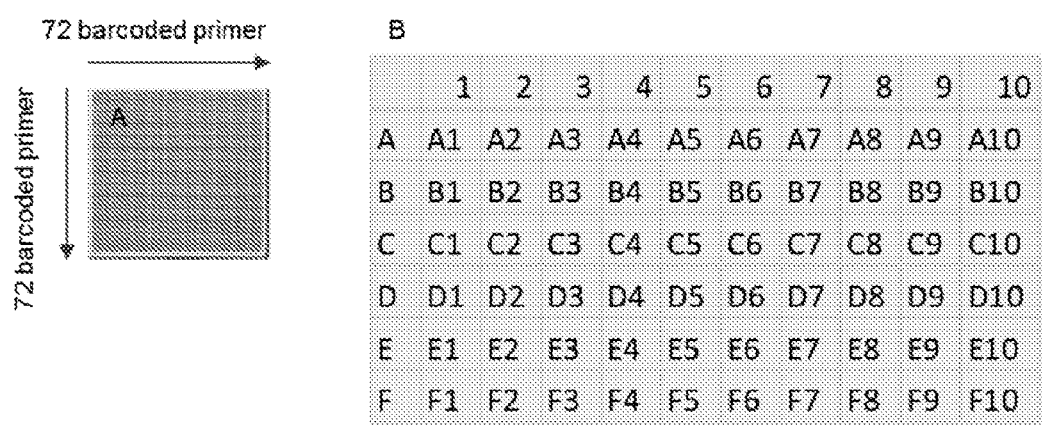
FIG. 4 shows an exemplary labeling scheme for a 72×72 well layout that may be employed with the methods, systems and compositions disclosed herein. (A) First primers, each distinctly-barcoded according to the column of well, and second primers, each distinctly-barcoded according to the row of well, are dispensed into each well. (B) An exemplary 10×6 matrix of the grid of (A). All 60 wells of the matrix are uniquely labeled (e.g., C7, F6, etc.) using only 16 primers (A-F and 1-10).

FIG. 4 describes a method for using only 144 barcodes to give a unique identity to 5184 wells in a 72×72 grid (e.g., a SMARTCHIP). In this example, each well is contacted with a first primer that is uniquely-barcoded to identify the row of the well and a second primer that is uniquely-barcoded to identify the column of the well. Using this system, whether the primers used are otherwise the same or not, nucleic acids amplified in each well will be uniquely labeled with a signature barcode sequence identifying the column and row from which the nucleic acid was derived. Such techniques are not limited to a 72×72 grid; rather, any grid or grid-like (e.g., offset grid (e.g., columns and or rows not aligned, zig-zag, etc.), etc.) arrangement of any suitable dimensions (e.g., 4×4, 12×16, 2×96, 100×100, 32×64, etc.) may find use in embodiments herein. In FIG. 4B, the column-specific barcodes are denoted by numbers (e.g., numbers which would correspond in practice to a nucleotide sequence) and row-specific barcodes are denoted by letters (e.g., numbers which would correspond in practice to a nucleotide sequence). As can be seen for the exemplary 6×10 portion of the wells, each of the 60 wells has a column-specific and a well-specific barcode, providing well-specific identifiers, using only 16 barcode sequences. For example, row "D" has the following combinations of barcodes: D1, D2, D3, D4, D5, D6, D7, D8, D9, and D10, and column "5" has the following combinations of barcodes: A5, B5, C5, D5, E5, and F5—where "D" is row specific barcode, and "5" is a column specific barcode.

G. Reagents and Assays

Reagents may be pre-dispensed into the reaction vessel (e.g., wells of the multi-well device), or added after a cell or cells are added to a well. In certain embodiments, the second 3'-blocked primer pair is pre-dispensed into the reaction vessel. Reagents contained within the liquid in the multi-well device depend on the reaction that is to be run with the single cell (or multiple cells) that is deposited into each well. In an embodiment, primer pairs are dispensed into a well and then dried, such as by freezing. The user can then selectively dispense, such as nano-dispense, the sample, probe and/or polymerase.

In some embodiments cells are subjected (e.g., after lysis and/or other processing steps) to amplification and/or sequencing analysis. Conducting one or more amplification reactions may comprise one or more PCR-based amplifications, non-PCR based amplifications, or a combination thereof. Illustrative non-limiting examples of nucleic acid amplification techniques include, but are not limited to, polymerase chain reaction (PCR), reverse transcription polymerase chain reaction (RT-PCR), nested PCR, linear amplification, multiple displacement amplification (MDA), real-time SDA, rolling circle amplification, circle-to-circle amplification transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to permit exponential increase in copy numbers of target nucleic acids. In a variation called RT-PCR, reverse transcriptase (RT) is used to make a complementary DNA (cDNA) from RNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., Proc. Natl. Acad. Sci. USA 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPaS to produce a duplex hemi-phosphorothioated primer extension product, endonuclease-mediated nicking of a hemi-modified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., BioTechnol. 6: 1197 (1988), herein incorporated by reference in its entirety), commonly referred to as Qβ replicase; a transcription based amplification method (Kwoh et al., Proc. Natl. Acad. Sci. USA 86:1173 (1989)); and, self-sustained sequence replication (Guatelli et al., Proc. Natl. Acad. Sci. USA 87: 1874 (1990), each of which is herein incorporated by reference in its entirety). For further discussion of known amplification methods see Persing, David H., "In Vitro Nucleic Acid Amplification Techniques" in Diagnostic Medical Microbiology: Principles and Applications (Persing et al., Eds.), pp. 51-87 (American Society for Microbiology, Washington, D.C. (1993)).

In some embodiments, nucleic acid sequencing methods are utilized (e.g., for detection of amplified nucleic acids). In some embodiments, the technology provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), semiconductor sequencing, massive parallel clonal, massive parallel single molecule SBS, massive parallel single molecule real-time, massive parallel single molecule real-time nanopore technology, etc. Morozova and Marra provide a review of some such technologies in Genomics, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are suitable, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. Nos. 6,432,360, 6,485,944, 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. Nos. 6,787,308; 6,833,246; herein incorporated by reference in their entireties), the Lynx massively parallel signature sequencing technology (Brenner et al. (2000). Nat. Biotechnol. 18:630-634; U.S. Pat. Nos. 5,695,934; 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., Clinical Chem., 55: 641-658, 2009; MacLean et al., Nature Rev. Microbiol., 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), Life Technologies/Ion Torrent, the Solexa platform commercialized by Illumina, GnuBio, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

In pyrosequencing (Voelkerding et al., Clinical Chem., 55: 641-658, 2009; MacLean et al., Nature Rev. Microbiol., 7: 287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., Clinical Chem., 55: 641-658, 2009; MacLean et al., Nature Rev.

Microbiol., 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 250 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbiol., 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specific color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology finds use in nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the technology finds use in HeliScope by Helicos BioSciences (Voelkerding et al., Clinical Chem., 55: 641-658, 2009; MacLean et al., Nature Rev. Microbiol., 7: 287-296; U.S. Pat. Nos. 7,169,560; 7,282,337; 7,482,120; 7,501,245; 6,818,395; 6,911,345; 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics is used. The per-base accuracy of the Ion Torrent sequencer is ~99.6% for 50 base reads, with ~100 Mb to 100 Gb generated per run. The read-length is 100-300 base pairs. The accuracy for homopolymer repeats of 5 repeats in length is ~98%. The benefits of ion semiconductor sequencing are rapid sequencing speed and low upfront and operating costs.

The technology finds use in another nucleic acid sequencing approach developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other single molecule sequencing methods include real-time sequencing by synthesis using a VisiGen platform (Voelkerding et al., *Clinical Chem.*, 55: 641-58, 2009; U.S. Pat. No. 7,329,492; U.S. patent application Ser. Nos. 11/671, 956; 11/781,166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

Reagents for any suitable type of assay may be added to the wells of the multi-well chip (e.g., using a multi-well dispenser, such as the one from WAFERGEN BIOSYSTEMS). Such reagents may be added to the wells before or after a cell (e.g., a single cell) is added to a well. In certain embodiments, protein detection assay components (e.g., anti-body based assays) are added to the wells. In other embodiments, SNP detection assay components are added to the wells. In other embodiments, nucleic acid sequencing assay components are added to the wells. In certain embodiments, nucleic acid sequence assay components that employ barcoding for labelling individual mRNA molecules, and/or for labeling for cell/well source (e.g., if wells pooled before sequencing analysis), and/or for labeling particular multi-well chips (e.g., if wells from two or more multi-well chips are pooled prior to sequencing) are employed. Examples of such barcoding methodologies and reagents are found in Pat. Pub. US2007/0020640, Pat. Pub. 2012/0010091, U.S. Pat. Nos. 8,835,358, 8,481,292, Qiu et al. (Plant. Physiol., 133, 475-481, 2003), Parameswaran et al. (Nucleic Acids Res. 2007 October; 35(19): e130), Craig et al. reference (Nat. Methods, 2008, October, 5(10):887-893), Bontoux et al. (Lab Chip, 2008, 8:443-450), Esumi et al. (Neuro. Res., 2008, 60:439-451), Hug et al., J. Theor., Biol., 2003, 221: 615-624), Sutcliffe et al. (PNAS, 97(5):1976-1981; 2000), Hollas and Schuler (Lecture Notes in Computer Science Volume 2812, 2003, pp 55-62), and WO201420127; all of which are herein incorporated by reference in their entireties, including for reaction conditions and reagents related to barcoding and sequencing of nucleic acids.

In certain embodiments, the barcode tagging and sequencing methods of WO2014201272 ("SCRB-seq" method) are employed. The necessary reagents for the SCRB-seq method (e.g., modified as necessary for small volumes) are added to the wells of the multi-well chips (e.g., where the single cell in the well has been lysed). Briefly, the SCRB-seq method amplifies an initial mRNA sample from a single cell in multi-well plates (as described above), where each well has a single cell. Initial cDNA synthesis uses a first primer with: i) N6 or N11 for cell/well identification, ii) N10 for particular molecule identification, iii) a poly T stretch to bind mRNA, and iv) a region that creates a region where a second template-switching primer will hybridize. The second primer is a template switching primer with a poly G 3' end, and 5' end that has iso-bases. After cDNA amplification, the tagged cDNA single cell/well samples are pooled. Then full-length cDNA synthesis occurs with two different primers, and full-length cDNA is purified. Next, a NEXTERA sequencing library is prepared using an i7 primer (adds one of 12 i7 tags to identify particular multi-well plates) and P5NEXTPT5 to add P5 tag for NEXTERA sequencing (P7 tag added to other end for NEXTERA). The library is purified on a gel, and then NEXTERA sequencing occurs. As a non-liming example, with twelve i7 plate tags, and 384 cell/well-specific barcodes, this allows total of 4,608 single cell transciptomes to be done at once. This method allows for quantification of mRNA transcripts in single cells and allows users to count the absolute number of transcript molecules/cell to remove any variables from normalization.

In further embodiments image and chip mapped wells within the chip are dynamically and/or statically selected for further analysis by a combination of single or multiple addition of reagents for detection and/or resolution of nucleic acids or lipids or carbohydrates or protein cell components reagents.

H. Kits

Aspects of the present disclosure also include compositions and kits. The compositions and kits may include, e.g., one or more of any of the reaction mixture components described above with respect to the subject methods. For example, the compositions and kits may include a nucleic acid sample (e.g., an RNA sample, a combined RNA and DNA sample, etc.), an amplification polymerase (e.g., a thermostable polymerase, etc.), a reverse transcriptase (e.g., a reverse transcriptase capable of template-switching, etc.), a template switch oligonucleotide, a first strand cDNA primer, one or more pairs of blocked amplification primers, dNTPs, a salt, a metal cofactor, one or more nuclease inhibitors (e.g., an RNase inhibitor and/or a DNase inhibitor), one or more molecular crowding agents (e.g., polyethylene glycol, or the like), one or more enzyme-stabilizing components (e.g., DTT), or any other desired kit component (s). In certain instances, the provided kits may include one or more components for performing a template-switching reverse transcription reaction. Such components include but are not limited to those described herein including e.g., a template switching oligonucleotide, a primer, a reverse transcriptase, etc. In certain embodiments, the kits include reagents for isolating nucleic acids from a nucleic acid source of interest.

In some instances, components of the subject compositions and/or kits may be presented as a "cocktail" where, as used herein, a cocktail refers to a collection or combination of two or more different but similar components in a single vessel. Components of the kits may be present in separate containers, or multiple components may be present in a single container, as desired. The subject compositions may be present in any suitable environment. According to one embodiment, the composition is present in a reaction tube (e.g., a 0.2 mL tube, a 0.6 mL tube, a 1.5 mL tube, or the like) or a well or microfluidic chamber or droplet or other suitable container. In certain aspects, the composition is present in two or more (e.g., a plurality of) reaction tubes or wells (e.g., a plate, such as a 96-well plate, a multi-well plate, e.g., containing about 1000, 5000, or 10,000 or more wells). The tubes and/or plates may be made of any suitable material, e.g., polypropylene, or the like, PDMS, or aluminum. The containers may also be treated to reduce adsorption of nucleic acids to the walls of the container. In certain aspects, the tubes and/or plates in which the composition is present provide for efficient heat transfer to the composition (e.g., when placed in a heat block, water bath, thermocycler, and/or the like), so that the temperature of the composition may be altered within a short period of time, e.g., as necessary for a particular enzymatic reaction to occur. According to certain embodiments, the composition is present in a thin-walled polypropylene tube, or a plate having thin-walled polypropylene wells or materials such as aluminum having high heat conductance.

In addition to the above-mentioned components, a subject kit may further include instructions for using the components of the kit, e.g., to practice the subject methods as described above. The instructions are generally recorded on a suitable recording medium. The instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, Hard Disk Drive (HDD) etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following examples are offered by way of illustration and not by way of limitation.

EXPERIMENTAL

Example 1

Using Blocked Primers with Polynucleotide Kinase

This example describes experimental data testing the unblocking of blocked primers with a titrated amount of polynucleotide kinase (PNK), where the blocked primers are used in a first round of PCR (PCR1). Ten samples of human brain total RNA were obtained. A reverse transcription and template switching reaction was performed for each sample using 2 µL of SMARTScribe™ reverse transcriptase (Takara Bio USA, Mountain View, Calif.) at 100 U/µL. The samples were cleaned up with ExoI nuclease (Zymo Research, Irvine, Calif.). The samples were pooled. 25% of the pooled reverse transcription sample was used as a template for subsequent PNK reaction samples.

Figure 6:
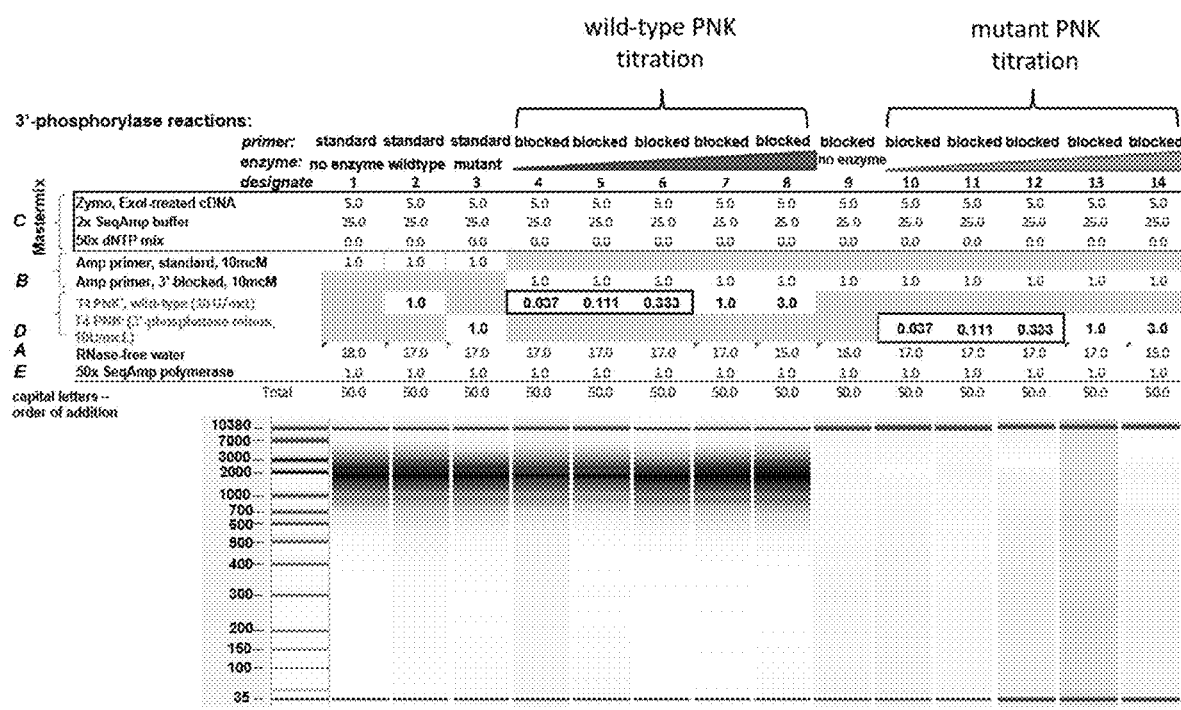
FIG. 6 shows the conditions employed and results obtained in Example 1 of the Experimental section, below.

The pooled samples were then split into control or titration reactions as shown in FIG. 6. The control reactions included unblocked standard primers while the PNK and PNK mutant reactions included blocked primers. Reactions 1-14 were generated as shown in FIG. 6. (numbers represent microliters added to the reaction sample, e.g., 50 µL total). Reagents were added in the order of Rnase-free water, amplification primer (either standard for the controls or blocked from a 10 µM stock), mastermix including target cDNA, buffer, and dNTPs, PNK (either wild-type for reactions 4-8 or mutant for reactions 10-14), and then SeqAmp™ polymerase (Takara Bio USA, Mountain View, Calif.). The PNK was added from a 10 unit/µL stock. The PNK was titrated to cover an 81-fold concentration range.

The reactions were subjected to a PNK treatment and subsequent PCR amplification reaction. The PNK treatment reaction included treatment at 37° C. for 30 minutes. The PCR amplification reaction included 1 minute at 95° C., 18 cycles of 98° C. for 10 seconds, 65° C. for 30 seconds, and 68° C. for 3 minutes, 10 minutes at 72° C., and hold at 4° C.

Reactions were run on a bioanalyzer (Agilent). Control reactions 1-3 indicated that regardless of whether PNK, PNK mutant, or no PNK enzyme was used, standard primers generated an amplification product. Reactions 4-8 produced an amplification product consistent with PNK cleaving the blocking group on the primer and activating the primers for amplification. Reactions 10-14 that included the mutant PNK were unable to generate a product, indicating that the PNK enzyme is specifically targeting the blocking group on the primers. Control reaction 9 did not generate a product indicating that in the absence of PNK enzyme, the blocked primers remain blocked and that the PNK mutant had nearly no enzymatic activity.

The results of this experiment demonstrate that the PNK enzyme specifically cleaves blocked primers to unblock them and thereby generate primers that are functional for a PCR amplification reaction.

Example 2

Use of Blocked Primers for Whole Genome Amplification on an ICELL8 System

This example describes an embodiment of blocked primers that can be used for whole genome amplification on an ICELL8™ single-cell analysis system (WaferGen, Fremont, Calif.). An ICELL8™ chip having 5,184 wells is obtained. The wells are pre-printed with barcoded primers. The barcoded primers include a unique barcode identifying each well in the chip. The barcodes are arrayed in a 72×72 matrix such that each of the 72 rows contains primers with different barcodes from each other and each of the 72 columns contains primers with different barcodes from each other. The barcodes in the rows are different from the barcodes in the columns. Together, the 72×72 barcoded primers result in 5,184 unique barcodes—one for each well of the ICELL8™ chip. The barcoded primers additionally include a blocking modification, i.e., a 3' phosphorylated end. The 3' phosphate prevents amplification of the primers, but can be removed with in an enzymatic step, e.g., exposure to PNK, such as described in Example 1 above, to activate the primers.

Single cells are deposited in the chip using a dispenser such that on average a single cell is deposited in a well according to Poisson statistics. In some instances, about 37% of the wells on the chip end up having a single cell. The single cell, including its nucleus, is lysed to release genomic DNA (hereinafter referred to as "genomic target DNA").

A dispensing step is performed on the wells to dispense whole genome amplification primers, i.e., the whole genome amplification primers of the PicoPLEX™ WGA Kit (Rubicon Genomics). The genomic target DNA is subjected to an amplification reaction to generate amplified genomic target DNA.

A second dispensing step is performed to add in polynucleotide kinase (PNK) to cleave the 3' phosphate on the barcoded primers, thereby activating the primers for amplification.

The amplified genomic target DNA is then amplified with the activated barcoded primers, thereby barcoding genomic DNA from each well. The barcoded genomic DNA is then pooled together for downstream processing, such as library preparation (e.g., attachment of flowcell sequencing adaptors) and sequencing.

Notwithstanding the appended claims, the disclosure is also defined by the following clauses:

1. A method comprising:
(a) providing a blocked primer reaction mixture comprising:
 (i) a blocked primer; and
 (ii) a template nucleic acid component from a single cell;
(b) unblocking the blocked amplification primer to produce an activated primer reaction mixture; and
(c) subjecting the activated primer reaction mixture to template dependent primer extension reaction conditions.

2. The method according to Clause 1, wherein the blocked primer comprises a thermally labile blocking moiety and the unblocking comprises heating the blocked primer reaction mixture.

3. The method according to Clause 1, wherein the blocked primer comprises an enzymatically labile blocking moiety and the unblocking comprises enzymatically removing the blocking moiety.

4. The method according to Clause 1, wherein the blocked primer comprises a light labile blocking moiety and the unblocking comprises exposing the blocked primer reaction mixture to light sufficient to remove the blocking moiety.

5. The method according to any of the preceding clauses, wherein the blocked primer is a member of a pair of blocked amplifications primers.

6. The method according to Clause 5, wherein the template mediated primer extension reaction conditions comprise nucleic acid amplification conditions.

7. The method according to any of the preceding clauses, wherein the nucleic acid amplification conditions comprise thermal cycling.

8. The method according to any of the preceding clauses, wherein the method produces amplified amounts of a template mediated primer extension reaction product.

9. The method according to any of the preceding clauses, wherein the template nucleic acid component comprises a plurality of nucleic acids.

10. The method according to Clause 9, wherein the plurality of nucleic acids comprise ribonucleic acids.

11. The method according to Clause 9, wherein the plurality of nucleic acids comprise deoxyribonucleic acids.

12. The method according to any of the preceding clauses, wherein the method comprises producing the template nucleic acid component.

13. The method according to Clause 12, wherein the template nucleic acid component is produced by obtaining a single cell and lysing the obtained single cell.

14. The method according to any of the preceding clauses, wherein the method is performed in a well.

15. The method according to Clause 14, wherein the method comprises producing the blocked primer reaction mixture by introducing a single cell into a well comprising the blocked primer and lysing the introduced single cell.

16. The method according to Clause 14, wherein the blocked primer in the well is dried.

17. The method according to any of the preceding clauses, wherein the method further comprises performing a second template mediated primer extension reaction.

18. The method according to Clause 17, wherein the second template mediated primer extension reaction is performed with an activated primer produced by unblocking a second blocked primer that is differentially blocked from the first blocked primer.

19. The method according to Clauses 17 or 18, wherein the second blocked primer is a member of a second pair of blocked amplification primers and the method comprises unblocking the second pair of blocked amplification primers and then using the unblocked second pair of amplification primers in a second nucleic acid amplification.

20. A method comprising:
 (a) introducing a template ribonucleic acid component of a single cell into a reaction vessel comprising a second pair of blocked amplification primers;
 (b) introducing into the reaction vessel:
  i) a reverse-transcriptase;
  ii) a first strand nucleic acid primer;
  iii) a thermostable polymerase; and
  iv) a first pair of amplification primers;
 (c) incubating the reaction vessel under conditions sufficient to synthesize cDNA from the template nucleic ribonucleic acid component using the a first strand nucleic acid primer primer and the reverse transcriptase;
 (d) amplifying the cDNA in the reaction vessel using the first pair of amplification primers to produce a first amplification product composition;
 (e) unblocking the second pair of blocked amplification primers to produce a second pair of active primers; and
 (f) amplifying the first amplification product composition with the second pair of active primers to produce a second amplification product composition.

21. The method according to Clause 18, wherein the first strand nucleic acid primer comprises ribonucleotides.

22. The method according to any of Clauses 20 to 21, wherein the first pair of amplification primers comprises blocked primers that are differentially blocked from the second pair of blocked amplification primers.

23. The method according to any of Clauses 20 to 22, wherein the second pair of blocked amplification primers comprises primers blocked with an enzymatically labile blocking moiety.

24. The method according to any of Clauses 20 to 23, wherein the second pair of blocked amplification primers comprises primers blocked with a light labile blocking moiety.

25. The method according to any of Clauses 22 to 24, wherein the blocked primers of the first pair of amplification primers comprise a thermally labile blocking moiety.

26. The method according to any of Clauses 20 to 25, wherein the amplifying step (d) comprises thermo-cycling.

27. The method according to any of Clauses 20 to 26, wherein the amplifying step (f) comprises thermo-cycling.

28. The method according to any of Clauses 20 to 27, wherein the introducing step (b) further comprises introducing a template switch oligonucleotide into the reaction vessel.

29. The method according to any of Clauses 20 to 28, wherein the introducing step (a) comprises introducing a single cell into the reaction vessel and then lysing the single cell in the reaction vessel.

30. The method according to any of Clauses 20 to 29, wherein the reaction vessel is a well that is part of a multi-well device comprising a plurality of wells.

31. The method according to any of Clauses 20 to 30, wherein the single cell is a T-cell.

32. The method according to Clause 31, wherein the first pair of amplification primers comprises a primer that hybridizes to an encoding sequence of a T-cell receptor constant region.

33. The method according to any of Clauses 20 to 32, wherein the method further comprises sequencing one or more nucleic acids of the second amplification product composition.

34. The method according to Clause 33, wherein the sequencing is performed by a next generation sequencing protocol.

35. The method according to Clause 34, wherein each member of the second pair of amplification primers comprises a sequencing adaptor.

36. A method comprising:
 (a) introducing a template nucleic acid component into a reaction vessel comprising a second pair of blocked amplification primers;

(b) introducing into the reaction vessel:
  i) a reverse-transcriptase;
  ii) a first strand nucleic acid primer;
  iii) a thermostable polymerase; and
  iv) a first pair of blocked amplification primers comprising primers that are differentially blocked from the second pair of blocked amplification primers;
(c) incubating the reaction vessel under conditions sufficient to synthesize cDNA from the template nucleic ribonucleic acid component using the a first strand nucleic acid primer and the reverse transcriptase;
(d) unblocking the first pair of blocked amplification primers to produce a first pair of active amplification primers;
(e) amplifying the cDNA in the reaction vessel using the first pair of active amplification primers to produce a first amplification product composition;
(f) unblocking the second pair of blocked amplification primers to produce a second pair of active amplification primers; and
(g) amplifying the first amplification product composition with the second pair of active amplification primers to produce a second amplification product composition.

37. The method according to Clause 36, wherein the first strand nucleic acid primer comprises ribonucleotides.

38. The method according to any of Clauses 36 to 37, wherein the second pair of blocked amplification primers comprises primers blocked with an enzymatically labile blocking moiety.

39. The method according to any of Clauses 36 to 37, wherein the second pair of blocked amplification primers comprises primers blocked with a light labile blocking moiety.

40. The method according to any of Clauses 36 to 39, wherein the blocked primers of the first pair of amplification primers comprise a thermally labile blocking moiety.

41. The method according to any of Clauses 36 to 39, wherein the introducing step (b) further comprises introducing a template switch oligonucleotide into the reaction vessel.

42. The method according to any of Clauses 36 to 41, wherein the introducing step (a) comprises introducing a template nucleic acid component of a single cell.

43. The method according to Clause 42, wherein the introducing step (a) comprises introducing a single cell into the reaction vessel and then lysing the single cell in the reaction vessel.

44. The method according to any of Clauses 36 to 43, wherein the reaction vessel is a well that is part of a multi-well device comprising a plurality of wells.

45. The method according to any of Clauses 36 to 44, wherein the method further comprises sequencing one or more nucleic acids of the second amplification product composition.

46. The method according to Clause 45, wherein the sequencing is performed by a next generation sequencing protocol.

47. A device comprising:
  a reaction vessel; and
  a pair of blocked amplification primers in the reaction vessel.

48. The device according to Clause 47, wherein the blocked amplification primers comprise a thermally labile blocking moiety.

49. The device according to Clause 47, wherein the blocked amplification primers comprise an enzymatically labile blocking moiety.

50. The device according to Clause 47, wherein the blocked amplification primers comprise a light labile blocking moiety.

51. The device according to any of Clauses 47 to 50, wherein the blocked amplification primers comprise a barcode.

52. The device according to any of Clauses 47 to 51, wherein the blocked amplification primers comprises a sequencing adaptor.

53. The device according to any of Clauses 47 to 52, wherein the blocked amplification primers are dried.

54. The device according to any of Clauses 47 to 53, wherein the reaction vessel is a well that is part of a multi-well device comprising a plurality of wells.

55. A method comprising:
  a) providing a reaction vessel containing a second primer pair comprising 3'-blocked ends that are enzyme-labile;
  b) dispensing a plurality of purified RNA sequences or at least one cell to said well, wherein said at least one cell is lysed to release a plurality of cell RNA sequences if said at least one cell is added to said well;
  c) dispensing into said reaction vessel: i) a reverse-transcriptase (RT) enzyme, ii) a thermostable polymerase, iii) an RNA primer that is generally non-extendable by said thermostable polymerase, and iv) a first primer pair comprising 3'-blocked ends that are thermo-labile;
  d) incubating said reaction vessel under conditions such that cDNA is synthesized from at least one of said plurality of purified or cell RNA sequences using said RNA primer and said RT enzyme;
  e) thermocycling said reaction vessel under conditions such that: i) said 3'-blocked ends of said first primer pair become 3'-unblocked ends due to a temperature increase, and ii) said first primer pair and said thermostable polymerase amplify said cDNA to generate first double-stranded amplification products;
  f) dispensing an enzyme to said reaction vessel such that said enzyme causes said 3'-blocked ends of said second primer pair to become 3'-unblocked ends; and
  g) thermocycling said reaction vessel under conditions such that said first double-stranded PCR products are amplified using said second primer pair to generate second double-stranded amplification products.

56. The method according to Clause 55, wherein said reaction vessel is a well, and said well is part of a multi-well device comprising a plurality of wells.

57. The method according to Clause 56, wherein said plurality of wells all have a second primer pair comprising 3' blocked ends that are enzyme-labile, and wherein steps b) through g) are conducts in all of said plurality of wells.

58. The method according to any of Clauses 55 to 57, wherein said enzyme in step f) comprises a T4 polynucleotide kinase.

59. The method according to any of Clauses 55 to 58, wherein a plurality of purified RNA sequences are dispensed in step b).

60. The method according to any of Clauses 55 to 59, wherein at least one cell is dispensed in step b), and said reaction vessel is treated such that said at least one cell is lysed releasing said plurality of cell RNA.

61. The method according to any of Clauses 55 to 60, wherein said RT enzyme adds a plurality of non-templated nucleotides upon reaching the 5' end of each mRNA template when said cDNA is synthesized.

62. The method according to Clause 61, wherein said dispensing in step c) further includes v) a template switching oligonucleotide that hybridizes to said non-templated nucleotides such that it is incorporated into said cDNA.

63. The method according to Clause 62, wherein said first primer pair comprises a first primer and a second primer, and wherein said first primer hybridizes to said template switching oligonucleotide that is part of said cDNA during said PCR amplifying in step e).

64. The method according to Clause 63, wherein said first primer comprises a well-specific barcode sequence, and said second primer comprises a UMI molecule specific sequence.

65. The method according to any of Clauses 55 to 64, wherein said second primer pair comprises a third primer and a fourth primer, wherein said third primer comprises a first plate-specific sequence and a first sequencing adaptor sequence, and said fourth primer comprises a second plate-specific sequence a second sequencing adaptor sequence.

66. The method according to any of Clauses 55 to 65, wherein said thermostable polymerase comprises Taq polymerase.

67. The method according to any of Clauses 55 to 66, wherein said RNA primer comprises at least two ribonucleotides at the 3' end.

68. The method according to any of Clauses 55 to 67, wherein said dispensing in step 0 further comprises adding additional thermostable polymerase.

69. The method according to any of Clauses 55 to 68, wherein said RNA primer comprises at least 3 ribonucleotides at the 3' end.

70. The method according to any of Clauses 55 to 69, where said first primer pair comprises a first primer and a second primer, wherein said second primer hybridizes to an encoding sequence of a constant region of a T-cell receptor (TCR).

71. The method according to any of Clauses 55 to 70, wherein said plurality of purified or cell RNA sequences are from a T-cell.

72. The method according to any of Clauses 55 to 71, further comprising h) sequencing said second-double stranded PCR products.

73. The method according to Clause 72, wherein said sequencing reveals the T-cell receptor variant diversity from said at least one cell.

74. A system comprising:
    a) a first primer pair comprising 3'-blocked ends that are thermo-labile;
    b) a RNA primer with at least two ribonucleotides at the 3' end,
    c) a second primer pair comprising 3'-blocked ends that are enzyme-labile; and
    d) an enzyme capable of un-blocking said 3'-blocked ends of said second primer pair.

75. The system of according to Clause 74, further comprising a thermostable polymerase that is unable to extend said RNA primer.

76. The system according to any of Clauses 74 to 75, further comprising: e) a plurality of purified RNA sequences.

77. The system according to any of Clauses 74 to 76, further comprising at least one isolated cell.

78. The system according to Clause 77, wherein said at least one isolated cell is a T-cell.

79. The system according to any of Clauses 74 to 78, further comprising a multi-well device.

80. The system according to any of Clauses 74 to 79, further comprising a thermocycler.

81. The system according to any of Clauses 74 to 80, further comprising a robotic dispensing system.

82. A composition comprising:
    a) a first primer pair comprising 3'-blocked ends that are thermo-labile;
    b) an RNA primer with at least two ribonucleotides at the 3' end,
    c) a second primer pair comprising 3'-blocked ends that are enzyme-labile; and
    d) an enzyme capable of un-blocking said 3'-blocked ends of said second primer pair.

83. A method comprising:
    a) providing a reaction vessel containing a first primer pair comprising 3'-blocked ends that are enzyme-labile;
    b) dispensing a plurality of purified RNA sequences or at least one cell to said reaction vessel, wherein said at least one cell is lysed to release a plurality of cell RNA sequences if said at least one cell is added to said reaction vessel;
    c) dispensing into said reaction vessel: i) a reverse-transcriptase (RT) enzyme that adds a plurality of non-templated nucleotides during cDNA synthesis, ii) a thermostable polymerase, iii) an RNA primer that is generally non-extendable by said thermostable polymerase, and iv) a template switching oligonucleotide that is able to hybridize to said non-templated nucleotides and; and
    d) incubating said reaction vessel under conditions such that: i) cDNA is synthesized from at least one of said plurality of purified or cell RNA sequences using said RNA primer and said RT enzyme, wherein said cDNA includes said plurality of non-templated nucleotides, and ii) said template switching oligonucleotide hybridizes to said non-templates nucleotides such that it is incorporated into said cDNA;
    e) dispensing an enzyme into said reaction vessel such that said enzyme causes said 3'-blocked ends of said first primer pair to become 3'-unblocked ends; and
    f) thermocycling said reaction vessel under conditions such that said first primer pair and said thermostable polymerase amplify said cDNA to generate first double-stranded amplification products.

84. The method according to Clause 83, wherein said first primer pair comprises a first primer and a second primer, and wherein said first primer hybridizes to said template switching oligonucleotide that is part of said cDNA during said PCR amplifying in step e).

85. The method according to Clause 84, wherein said first primer comprises a well-specific barcode sequence, and said second primer comprises a UMI molecule specific sequence.

86. The method according to any of Clauses 83 to 85, wherein said first primer pair is in a pre-printed, dried format in said reaction vessel prior to said dispensing in step b).

87. The method according to any of Clauses 83 to 86, further comprising: g) adding a second primer pair to said reaction vessel, and thermocycling said reaction vessel under conditions such that said first double-stranded PCR products are amplified using said second primer pair to generate second double-stranded amplification products.

88. The method according to Clause 87, wherein said second primer pair comprises a third primer and a fourth primer, wherein said third primer comprises a first plate-specific sequence and a first sequencing adaptor sequence, and said fourth primer comprises a second plate-specific sequence a second sequencing adaptor sequence.

89. A system or composition comprising:
    a) a first primer pair comprising 3'-blocked ends that are enzyme-labile;
    b) an RNA primer with at least two ribonucleotides at the 3' end, c) a template switching oligonucleotide comprising a plurality of isoC and/or isoG nucleotides; and d) an enzyme capable of un-blocking said 3'-blocked ends of said first primer pair.

90. The system or composition according to Clause 89, further comprising: e) a reverse-transcriptase (RT) enzyme that adds a plurality of non-templated nucleotides during cDNA synthesis, wherein said template switching oligonucleotide is able to hybridize to said non-templated nucleotides.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. A method comprising:
   (a) combining a blocked primer comprising a light labile blocking moiety with a template nucleic acid component from a single cell to produce a blocked primer reaction mixture;
   (b) unblocking the blocked primer of the blocked primer reaction mixture by exposing the blocked primer reaction mixture to light sufficient to remove the blocking moiety to produce an activated primer reaction mixture; and
   (c) subjecting the activated primer reaction mixture to template dependent primer extension reaction conditions.

2. The method according to claim 1, wherein the blocked primer is a member of a pair of blocked amplifications primers.

3. The method according to claim 2, wherein the template dependent primer extension reaction conditions comprise nucleic acid amplification conditions.

4. The method according to claim 3, wherein the nucleic acid amplification conditions comprise thermal cycling.

5. The method according to claim 1, wherein the template nucleic acid component comprises a plurality of nucleic acids.

6. The method according to claim 5, wherein the plurality of nucleic acids comprise ribonucleic acids or deoxyribonucleic acids.

7. The method according to claim 1, wherein the method comprises producing the template nucleic acid component.

8. The method according to claim 7, wherein the template nucleic acid component is produced by obtaining a single cell and lysing the obtained single cell.

9. The method according to claim 1, wherein the method is performed in a well.

10. The method according to claim 9, wherein the method comprises producing the blocked primer reaction mixture by introducing a single cell into a well comprising the blocked primer and lysing the introduced single cell.

11. The method according to claim 10, wherein the blocked primer in the well is dried.

12. The method according to claim 1, wherein the method further comprises performing a second template mediated primer extension reaction.

13. The method according to claim 12, wherein the second template mediated primer extension reaction is performed with an activated primer produced by unblocking a second blocked primer that is differentially blocked from the first blocked primer.

14. The method according to claim 13, wherein the second blocked primer is a member of a second pair of blocked amplification primers and the method comprises unblocking the second pair of blocked amplification primers and then using the unblocked second pair of amplification primers in a second nucleic acid amplification.

15. A method comprising:
   (a) combining a blocked primer comprising a thermally labile blocking moiety with a template nucleic acid component from a single cell to produce a blocked primer reaction mixture;
   (b) unblocking the blocked primer of the blocked primer reaction mixture by heating the blocked primer reaction mixture to a temperature sufficient to remove the thermally labile blocking moiety to produce an activated primer reaction mixture; and
   (c) subjecting the activated primer reaction mixture to template dependent primer extension reaction conditions.

16. A method comprising:
   (a) combining a blocked primer comprising an enzymatically labile blocking moiety with a template nucleic acid component from a single cell to produce a blocked primer reaction mixture;
   (b) adding an enzyme to the blocked primer reaction mixture to enzymatically remove the enzymatically labile blocking moiety of the blocked primer, thereby unblocking the blocked primer of the blocked primer reaction mixture to produce an activated primer reaction mixture; and
   (c) subjecting the activated primer reaction mixture to template dependent primer extension reaction conditions.

17. The method according to claim 1, wherein the light labile blocking moiety is attached to the 3' end of the blocked primer.

18. The method according to claim 17, wherein the blocked primer further comprises a non-template sequence domain with a length of 10 to 40 nucleotides.

19. The method according to claim 16, wherein the method further comprises producing the template nucleic acid component.

20. The method according to claim 19, wherein the template nucleic acid component is produced by a polymerase mediated template dependent primer extension reaction.

21. The method according to claim 20, wherein the polymerase mediated template dependent primer extension reaction comprises a reverse transcriptase mediated template dependent primer extension reaction.

* * * * *